United States Patent [19]
Thatcher et al.

[11] Patent Number: 5,883,122
[45] Date of Patent: Mar. 16, 1999

[54] NITRATE ESTERS AND THEIR USE FOR NEUROLOGICAL CONDITIONS

[75] Inventors: Gregory R. J. Thatcher; Brian M. Bennett; James N. Reynolds; Roland J. Boegman; Khem Jhamandas, all of Kingston, Canada

[73] Assignee: Queen's University at Kingston, Kingston, Canada

[21] Appl. No.: 867,856

[22] Filed: Jun. 3, 1997

Related U.S. Application Data

[63] Continuation-in-part of Ser. No. 658,145, filed as PCT/CA97/00372, May 30, 1997, Pat. No. 5,807,847.

[51] Int. Cl.$^6$ .......................... A61K 31/21; A61K 31/39; A61K 31/66; C07C 203/04
[52] U.S. Cl. .......................... 514/509; 514/114; 514/439; 549/40; 558/14; 558/175; 558/446; 558/483; 558/484; 558/485; 558/87; 558/143
[58] Field of Search .............................. 549/40; 558/14, 558/175, 446, 483, 484, 485, 87, 143; 514/114, 439, 509

[56] References Cited

U.S. PATENT DOCUMENTS

| | | |
|---|---|---|
| 4,801,596 | 1/1989 | Simon et al. . |
| 4,863,949 | 9/1989 | Simon et al. . |
| 5,049,694 | 9/1991 | Bron et al. . |
| 5,284,872 | 2/1994 | Sandrock et al. . |
| 5,428,061 | 6/1995 | Sandrock et al. . |

FOREIGN PATENT DOCUMENTS

| | | |
|---|---|---|
| 764461 | 8/1967 | Canada . |
| 792246 | 8/1968 | Canada . |
| 2075988 | 8/1991 | Canada . |
| 2158368 | 9/1994 | Canada . |
| 51-125750 | 11/1976 | Japan . |
| 01-304353 | 12/1989 | Japan . |
| WO 94/06428 | 3/1994 | WIPO . |
| WO 95/00477 | 1/1995 | WIPO . |

OTHER PUBLICATIONS

Yang, K., Artz, J.D., Lock, J., Sanchez, C., Bennett, B.M., Fraser, A.B., and Thatcher, G.R.J., "Synthesis of novel organic nitrate esters: guanylate cyclase activation and tissue relaxation", *J. Chem. Soc., Perkin Trans. 1*, 1073–1075 (1996).

Artz, J.D., Yang, K., Lock, J., Sanchez, C., Bennett, B.M., and Thatcher, G.R.J., "Reactivity of thionitrate esters: putative intermediates in nitrovasodilator activity", *Chem. Commun.* 927–928 (1996).

Bennett, B.M., McDonald, B.J., Nigam, R., and Simon, W.C., "Biotransformation of organic nitrates and vascular smooth muscle cell function", *Trends in Pharmacol. Sci.* 15: 245–249 (1994).

Cameron, D.R., Borrajo, A.M.P., Bennett, B.M., and Thatcher, G.R.J., "Organic nitrates, thionitrates, peroxynitrites, and nitric oxide: a molecular orbital study of $RXNO_2 \leftarrow \rightarrow RXONO$ (X=O,S) rearrangement, a reaction of potential biological significance", *Can. J. Chem.* 73: 1627–1638 (1995).

Chong, S., and Fung, H.-L., "Biological and pharmacological interactions between nitroglycerin and thiols. Effects of thiol structure on nitric oxide generation and tolerance reversal", *Biochem. Pharm.*, 42: 1433–1439 (1991).

Feelisch, M., "Biotransformation to nitric oxide of organic nitrates in comparison to other nitrovasodilators", *Eur. Heart J.* 14(Supp. 1): 123–132 (1993).

Fung, H.-L., "Nitrate therapy: is there an optimal substance and formulation", *Eur. Heart J.,* 12(Supp A):9–12 (1991).

Kojda, G., Feelisch, M., and Noack, E., "Sulfhydryl–containing nitrate esters: a new class of nitric oxide donors", *Cardiovasc. Drug Rev.* 13: 275–288 (1995).

Yeates, R.A., "Possible mechanisms of activation of soluble guanylate cyclase by organic nitrates", *Arzneim–Forsch./Drug Res.* 42(II): 1314–1317 (1992).

Yeates, R.A., Laufen, H., and Leitold, M., "The reaction between organic nitrates and sulfhydryl compounds. A possible model system for the activation of organic nitrates.", *Mol. Pharm.* 28: 555–559 (1985).

Zanzinger, J., Feelisch, M., and Bassenge, E., "Novel organic nitrates are potent dilators of large coronary arteries with reduced development of tolerance during long–term infusion in dogs: role of the Sulfhydryl moiety", *J. Cardiovas. Pharm.* 23: 772–778 (1994).

*Primary Examiner*—Michael G. Ambrose
*Attorney, Agent, or Firm*—Richard J. Hicks; Carol Miernicki Steeg

[57] ABSTRACT

Aliphatic nitrate esters having a sulfur or phosphorus atom β or γ to a nitrate group and their congeners having efficacy as neuroprotective agents are described. Preferred nitrate esters may be synthesized by nitration of a 3-bromo-1,2-propanediol, and subsequent reaction to yield the desired mono-, di- or tetra-nitrate ester.

21 Claims, 15 Drawing Sheets

NITRATE ESTERS AND THEIR USE FOR NEUROLOGICAL CONDITIONS

CROSS REFERENCE TO RELATED APPLICATION

This application is a continuation in part of our earlier filed application, Ser. No. 08/658,145, filed as PCT/CA97/00372, May 30, 1997, now U.S. Pat. No. 5,807,847, the disclosure of which is incorporated herein by reference.

FIELD OF INVENTION

This invention relates to novel aliphatic nitrate esters and use thereof as neuroprotective agents. More particularly this invention relates to nitrate esters bearing a sulfur or phosphorus atom β or γ to a nitrate group and their congeners which have therapeutic utility as neuroprotective agents and/or cognition enhancers.

BACKGROUND OF INVENTION

The nitrate ester, glyceryl trinitrate (GTN) or nitroglycerin, has been used as a vasodilator in the treatment of angina pectoris for over a hundred years, and the dominant contemporary belief is that GTN exerts its therapeutic effect through in vivo release of nitric oxide (NO). Other organic nitrates, such as isosorbide dinitrate, have also been identified as effective and clinically important vasodilators. NO itself has been identified as Endothelium Derived Relaxing Factor (EDRF) and several classes of compounds, for example nitrosothiols, in addition to organic nitrates, have been proposed as NO donors or NO prodrugs. Well-known examples of these classes of compounds and GTN itself have been suggested to demonstrate neurotoxic or neuroprotective effects by dint of interactions with the redox modulatory site of the N-methyl-D-aspartate (NMDA) excitatory amino acid receptor. Thus GTN is firstly a potent vasodilator and secondly possesses neuroprotective properties. Several attempts have been made to increase the efficacy or potency of alternative nitrate esters as vasodilators relative to GTN, for example, by incorporation of propanolamine or cysteine functionalities. However, no attempt has been made to separately regulate the vasodilatory and neuroprotective effects of GTN. Indeed, postural hypertension, weakness and other signs of cerebral ischemia are adverse effects, associated with the vasodilatory effects of GTN and observed in treatment, which are highly contraindicative of GTN itself as a clinically useful neuroprotective therapeutic agent.

In as much as the potent vasodilatory effects of nitrate esters may prove (a) deleterious to or alternatively (b) synergistic with the neuroprotective effects of GTN, it is postulated herein that regulation of these two effects is required for development of new and useful neuroprotective therapeutic agents. Further, it is postulated that such regulation may be achieved through use of nitrate esters incorporating sulfur-containing or phosphorus-containing functionalities into the structure of the nitrate esters or through use of their congeners. Interaction of nitrate esters with amino acid neurotransmitter receptors, including the NMDA receptor, will provide examples of compounds with neuroprotective properties, but modulation of the γ-aminobutyric acid (GABA) receptor response will provide examples of nitrate esters capable of cognition enhancement. These postulates are based, in part, on bioassay data on such compounds. Thus, there is a need for synthetic aliphatic nitrate esters containing sulfur or phosphorus functionalities or their congeners as new and useful therapeutic agents for use in neuroprotection and/or cognition enhancement. It will be appreciated, therefore, that these compounds can be used for treatment of: stroke; Parkinson's disease; Alzheimer's disease; Huntington's disease; multiple sclerosis; amyotrophic lateral sclerosis; AIDS-induced dementia; epilepsy; alcoholism; alcohol withdrawal; drug-induced seizures; viral/bacterial/fever-induced seizures; trauma to the head; hypoglycemia; hypoxia; myocardial infarction; cerebral vascular occlusion; cerebral vascular hemorrhage; hemorrhage; environmental excitoxins of plant, animal and marine origin; dementias of all type, trauma, drug-induced brain damage, aging.

OBJECT OF INVENTION

It is an object of the present invention to provide novel aliphatic nitrate esters bearing a sulfur or phosphorus moiety β or γ to a nitrate group, or congeners thereof. Another object of the present invention is to provide methods for making the novel S- or P-containing nitrate esters and their novel congener nitrate esters. Yet another object of the present invention is to provide novel drugs for use as neuroprotective agents and/or cognition enhancers.

BRIEF DESCRIPTION OF INVENTION

By one aspect of this invention there is provided aliphatic nitrate esters containing at least one nitrate group, in which a S or P atom is situated β or γ to a nitrate group, or congeners thereof, having the general formula:

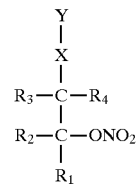

where X is $CH_2$, O, NH, NMe, CN, NHOH, $N_2H_3$, $N_2H_2R_{13}$, $N_2HR_{13}R_{14}$, $N_3$, S, SCN, $SCN_2H_2(R_5)_2$, $SCN_2H_3(R_5)$, $SC(O)N(R_5)_2$, $SC(O)NHR_5$, $SO_3M$, SH, $SR_7$, $SO_2M$, $S(O)R_8$, $S(O)_2R_9$, $S(O)OR_8$, $S(O)_2OR_9$, $PO_3M_2$, $P(O)(OR_5)(OR_6)$, $P(O)(OR_6)(OM)$, $P(O)(R_5)(OR_8)$, $P(O)(OM)R_5$, $CO_2M$, $CO_2H$, $CO_2R_{11}$, $C(O)$, $C(O)R_{12}$, $C(O)(OR_{13})$, $PO_2M$, $P(O)(OR_{14})$, $P(O)(R_{13})$, SO, $S_2$, $C(O)(SR_{13})$, $SR_4$, or $SSR_4$;

Y is SCN, $SCN_2H_2(R_5)_2$, $SC(O)NHR_5$, $SC(O)N(R_5)_2$, $SR_4$, $SR_{10}$, $SSR_{10}$, $SO_2M$, $SO_3M$, $PO_3HM$, $PO_3M_2$, $P(O)(OR_5)(OR_6)$, or $P(O)(OR_6)(OM)$, CN, $N_3$, $N_2H_2R_{13}$, $N_2HR_{13}R_{14}$, $CO_2M$, $CO_2H$, $CO_2R_{11}$, $C(O)R_{12}$, $C(O)(SR_{13})$, or does not exist;

$R_5$, $R_6$, $R_8$, $R_9$, $R_{10}$, $R_{12}$, $R_{13}$, $R_{14}$, $R_{15}$, $R_{16}$, are the same or different alkyls containing 1–12 carbon atoms which may contain 1–4 $ONO_2$ substituents or $C_1$ or $C_2$ connections to $R_1$–$R_3$ in cyclic derivatives;

$R_7$, $R_{11}$ are $C_1$–$C_8$, alkyl or acyl;

$R_2$ and $R_4$ are the same or different and selected from H, $ONO_2$, $C_1$–$C_4$ alkyl optionally bearing 1–3 nitrate groups, and acyl groups ($—C(O)R_{10}$);

$R_1$ and $R_3$ are the same or different and selected from H, $C_1$–$C_4$ alkyl and chains, which may include one O, linking $R_1$ and $R_3$ to form pentosyl, hexosyl, cyclopentyl or cycohexyl rings, which rings optionally bear hydroxyl substituents; and M is H, $Na^+$, $K^+$, $NH_4^+$ or $N^+H_nR_{11(4-n)}$ where n is 0–3; and with the proviso that, when X is O, Y is not $COR_{12}$, and with the proviso that, when $R_3$ is H, $R_6$ is not ethyl or n-butyl;

and pharmaceutically acceptable salts thereof.

By another aspect of this invention there is provided a pharmaceutical composition comprising an effective amount of an aliphatic nitrate ester having the formula:

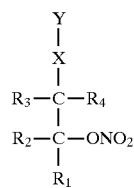

where X is $CH_2$, O, NH, NMe, CN, NHOH, $N_2H_3$, $N_2H_2R_{13}$, $N_2HR_{13}R_{14}$, $N_3$, S, SCN, $SCN_2H_2(R_5)_2$, $SCN_2H_3(R_5)$, $SC(O)N(R_5)_2$, $SC(O)NHR_5$, $SO_3M$, SH, $SR_7$, $SO_2M$, $S(O)R_8$, $S(O)_2R_9$, $S(O)OR_8$, $S(O)_2OR_9$, $PO_3M_2$, $P(O)(OR_5)(OR_6)$, $P(O)(OR_6)(OM)$, $P(O)(R_5)(OR_8)$, $P(O)(OM)R_5$, $CO_2M$, $CO_2H$, $CO_2R_{11}$, $C(O)$, $C(O)R_{12}$, $C(O)(OR_{13})$, $PO_2M$, $P(O)(OR_{14})$, $P(O)(R_{13})$, SO, $SO_2$, $C(O)(SR_{13})$, $SR_4$, or $SSR_4$;

Y is SCN, $SCN_2H_2(R_5)_2$, $SC(O)NHR_5$, $SC(O)N(R_5)_2$, $SR_4$, $SR_{10}$, $SSR_{10}$, $SO_2M$, $SO_3M$, $PO_3HM$, $PO_3M_2$, $P(O)(OR_5)(OR_6)$, or $P(O)(OR_6)(OM)$, CN, $N_3$, $N_2H_2R_{13}$, $N_2HR_{13}R_{14}$, $CO_2M$, $CO_2H$, $CO_2R_{11}$, $C(O)R_{12}$, $C(O)(SR_{13})$, or does not exist;

$R_5$, $R_6$, $R_8$, $R_9$, $R_{10}$, $R_{12}$, $R_{13}$, $R_{14}$, $R_{15}$, $R_{16}$, are the same or different alkyls containing 1–12 carbon atoms which may contain 1–4 $ONO_2$ substituents or $C_1$ or $C_2$ connections to $R_1$-$R_3$ in cyclic derivatives;

$R_7$, $R_{11}$ are $C_1$–$C_8$, alkyl or acyl;

$R_2$ and $R_4$ are the same or different and selected from H, $ONO_2$, $C_1$–$C_4$ alkyl optionally bearing 1–3 nitrate groups, and acyl groups (—$C(O)R_{10}$);

$R_1$ and $R_3$ are the same or different and selected from H, $C_1$–$C_4$ alkyl and chains, which may include one O, linking $R_1$ and $R_3$ to form pentosyl, hexosyl, cyclopentyl or cycohexyl rings, which rings optionally bear hydroxyl substituents; and M is H, $Na^+$, $K^+$, $NH_4^+$ or $N^+H_nR_{11(4-n)}$ where n is 0–3;

and with the proviso that, when X is O, Y is not $COR_{12}$, and with the proviso that, when $R_3$ is H, $R_6$ is not ethyl or n-butyl;

and the pharmaceutically acceptable salts thereof, in admixture with a physiologically acceptable carrier therefor.

By yet another aspect of this invention there is provided a method for effecting neuroprotection in a patient in need thereof comprising administering to said patient an effective amount of an aliphatic nitrate ester having the formula:

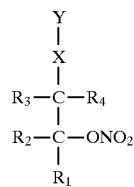

where X is $CH_2$, O, NH, NMe, CN, NHOH, $N_2H_3$, $N_2H_2R_{13}$, $N_2HR_{13}R_{14}$, $N_3$, S, SCN, $SCN_2H_2(R_5)_2$, $SCN_2H_3(R_5)$, $SC(O)N(R_5)_2$, $SC(O)NHR_5$, $SO_3M$, SH, $SR_7$, $SO_2M$, $S(O)R_8$, $S(O)_2R_9$, $S(O)OR_8$, $S(O)_2OR_9$, $PO_3M_2$, $P(O)(OR_5)(OR_6)$, $P(O)(OR_6)(OM)$, $P(O)(R_5)(OR_8)$, $P(O)(OM)R_5$, $CO_2M$, $CO_2H$, $CO_2R_{11}$, $C(O)$, $C(O)R_{12}$, $C(O)(OR_{13})$, $PO_2M$, $P(O)(OR_{14})$, $P(O)(R_{13})$, SO, $SO_2$, $C(O)(SR_{13})$, $SR_4$, or $SSR_4$;

Y is SCN, $SCN_2H_2(R_5)_2$, $SC(O)NHR_5$, $SC(O)N(R_5)_2$, $SR_4$, $SR_{10}$, $SSR_{10}$, $SO_2M$, $SO_3M$, $PO_3HM$, $PO_3M_2$, $P(O)(OR_5)(OR_6)$, or $P(O)(OR_6)(OM)$, CN, $N_3$, $N_2H_2R_{13}$, $N_2HR_{13}R_{14}$, $CO_2M$, $CO_2H$, $CO_2R_{11}$, $C(O)R_{12}$, $C(O)(SR_{13})$, or does not exist;

$R_5$, $R_6$, $R_8$, $R_9$, $R_{10}$, $R_{12}$, $R_{13}$, $R_{14}$, $R_{15}$, $R_{16}$, are the same or different alkyls containing 1–12 carbon atoms which may contain 1–4 $ONO_2$ substituents or $C_1$ or $C_2$ connections to $R_1$-$R_3$ in cyclic derivatives;

$R_7$, $R_{11}$, are $C_1$–$C_8$, alkyl or acyl;

$R_2$ and $R_4$ are the same or different and selected from H, $ONO_2$, $C_1$–$C_4$ alkyl optionally bearing 1–3 nitrate groups, and acyl groups (—$C(O)R_{10}$);

$R_1$ and $R_3$ are the same or different and selected from H, $C_1$–$C_4$ alkyl and chains, which may include one O, linking $R_1$ and $R_3$ to form pentosyl, hexosyl, cyclopentyl or cycohexyl rings, which rings optionally bear hydroxyl substituents; and M is $H$, $Na^+$, $K^+$, $NH_4^+$ or $N^+H_nR_{11(4-n)}$ where n is 0–3;

and with the proviso that, when X is O, Y is not $COR_{12}$, and with the proviso that, when $R_3$ is H, $R_6$ is not ethyl or n-butyl;

and pharmaceutically acceptable salts thereof.

DETAILED DESCRIPTION OF PREFERRED EMBODIMENTS

Figure 1:
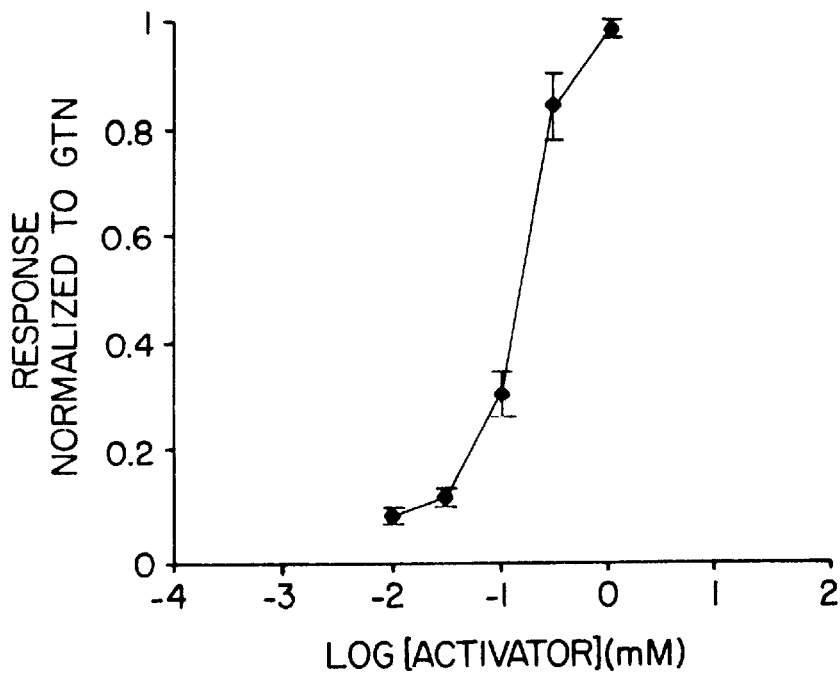
FIG. 1 is a graph showing the effect of GTN with added L-cysteine (2 mM) on soluble guanylyl cyclase (Gcase) activity in the 105,000 g supernatant fraction of rat aorta homogenate. Experimental incubations were performed at 37° C. for 10 min. Bars represent the mean ± standard errors calculated separately for each point.

Simple nitrate esters according to this invention contain one or more nitrate groups in which a S or P atom is situated $\beta$ or $\gamma$ to a nitrate group or their congeners. Accordingly, a general formula for the esters of this invention is:

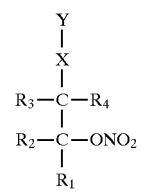

where X is $CH_2$, O, NH, NMe, CN, NHOH, $N_2H_3$, $N_2H_2R_{13}$, $N_2HR_{13}R_{14}$, $N_3$, S, SCN, $SCN_2H_2(R_5)_2$, $SCN_2H_3(R_5)$, $SC(O)N(R_5)_2$, $SC(O)NHR_5$, $SO_3M$, SH, $SR_7$, $SO_2M$, $S(O)R_8$, $S(O)_2R_9$, $S(O)OR_8$, $S(O)_2OR_9$, $PO_3M_2$, $P(O)(OR_5)(OR6)$, $P(O)(OR_6)(OM)$, $P(O)(R_5)(OR_8)$, $P(O)(OM)R_5$, $CO_2M$, $CO_2H$, $CO_2R_{11}$, C(O), $C(O)R_{12}$, $C(O)(OR_{13})$, $PO_2M$, $P(O)(OR_{14})$, $P(O)(R_{13})$, SO, $SO_2$, $C(O)(SR_{13})$, $SR_4$, or $SSR_4$;

Y is SCN, SCN$_2$H$_2$(R$_5$)$_2$, SC(O)NHR$_5$, SC(O)N(R$_5$)$_2$, SR$_4$, SR$_{10}$, SSR$_{10}$, SO$_2$M, SO$_3$M, PO$_3$HM, PO$_3$M$_2$, P(O)(OR$_5$)(OR$_6$), or P(O)(OR$_6$)(OM), CN, N$_3$, N$_2$H$_2$R$_{13}$, N$_2$HR$_{13}$R$_{14}$, CO$_2$M, CO$_2$H, CO$_2$R$_{11}$, C(O)R$_{12}$, C(O)(SR$_{13}$), or does not exist;

R$_5$, R$_6$, R$_8$, R$_9$, R$_{10}$, R$_{12}$, R$_{13}$, R$_{14}$, R$_{15}$, R$_{16}$, are the same or different alkyls containing 1–12 carbon atoms which may contain 1–4 ONO$_2$ substituents or C$_1$ or C$_2$ connections to R$_1$–R$_3$ in cyclic derivatives;

R$_7$, R$_{11}$, are C$_1$–C$_8$, alkyl or acyl;

R$_2$ and R$_4$ are the same or different and selected from H, ONO$_2$, C$_1$–C$_4$ alkyl optionally bearing 1–3 nitrate groups, and acyl groups (—C(O)R$_{10}$);

R$_1$ and R$_3$ are the same or different and selected from H, C$_1$–C$_4$ alkyl and chains, which may include one O, linking R$_1$ and R$_3$ to form pentosyl, hexosyl, cyclopentyl or cycohexyl rings, which rings optionally bear hydroxyl substituents; and M is H, Na$^+$, K$^+$, NH$_4^+$ or N$^+$H$_n$R$^{11(4-n)}$ where n is 0–3;

and with the proviso that, when X is O, Y is not COR$_{12}$, and with the proviso that, when R$_3$ is H, R$_6$ is not ethyl or n-butyl;

and the pharmaceutically acceptable salts thereof.

Compounds according to the present invention fall into nine main categories having the formulae:

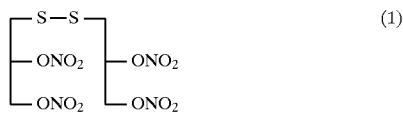 (1)

 (2)

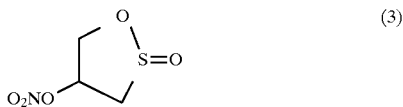 (3)

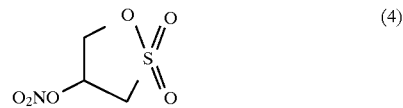 (4)

 (5)

 (6)

 (7)

 (8)

 (9)

The compound of formula 1 was synthesized via the Bunte salt (2). The synthesis of compound 2 proceeded from a 3-halopropane-1,2-diol by dropwise addition into a cold mixture of nitric acid (68–70%, 4.0 eq) and sulfuric acid (95%, 4.0 eq) in methylene chloride (50 mL) and reaction at room temperature for 30 minutes. The organic layer was separated, washed, dried and concentrated to yield a yellow oil which was purified by silica gel flash chromatography to give a 45% yield of 3-halopropane-1,2-diol dinitrate: either 3-bromopropane-1,2-diol dinitrate (compound 10) or 3-chloropropane-1,2-diol dinitrate (compound 11). The Bunte salt (compound 2) was prepared by reacting either nitrate 10 or 11 with an equimolar portion of Na$_2$S$_2$O$_3$ in 3:1 MeOH/H$_2$O at 50° C. for 10 hours and subsequently purifying by silica gel flash chromatography. The Bunte salt 2 was oxidized with a small molar excess of hydrogen peroxide H$_2$O$_2$ (30%) in an ethanol: water mixture (1: 1) with a catalytic amount of sulfuric acid for 2 days. Extraction with methylene chloride, concentration, and purification by silica gel flash chromatography yielded the tetranitrate (1): The $^{13}$C NMR spectra of compounds 1 and 2 revealed 6 and 3 signals respectively, as expected from the presence of two chiral centres in compound 1 and only one in compound 2 (Table 1). The Bunte salt mononitrate 8 was synthesized by an analogous method to the Bunte salt dinitrate 2, in this case, starting from 2-chloroethyl nitrate or 2-bromoethyl nitrate.

Nitration of bis-(2,3-dihydroxypropyl) disulfide in the biphasic CH$_2$Cl$_2$/aq. HNO$_3$/H$_2$SO$_4$, medium described above, yielded, after chromatographic silica gel purification, 10% and 5% yields of the sultine 3 and sultone 4, respectively. NMR spectra obtained for these products were highly solvent-dependent and were similar to those of the glycerol dinitrates, but with the significant difference that the large geminal coupling is associated with the upfield rather than the downfield methylene protons (Table 1). Definitive structure identification rested upon mass spectral data: soft chemical ionization with Cl– ion capture determined compounds 3 and 4 to be the sultine and sultone, respectively.

The compound of formula 5 was synthesized by two methods. In the first method, a 3-halopropane-1,2-diol was silylated to provide a substrate for the Arbuzov reaction with triethyl phosphite. The resulting phosphonate was nitrated using nitronium tetrafluoroborate to yield the product 5, which was isolated after silica flash chromatography. In the second method, an Arbuzov reaction with 1-halo-2,3-epoxypropane yielded the 1-phosphono-2,3-epoxypropane, which was converted to the dinitrate 5 using the same nitrating procedure detailed for synthesis of compound 1. Isolation after chromatography yielded the product 5 with: $^{31}$P NMR δ=23 ppm; $^{13}$C NMR δ=16, 27, 62, 71, 75 ppm; $^1$H NMR δ=1.3, 2.2, 4.1, 4.4–5.0, 5.5 ppm.

The compound of formula 6 was synthesized from bromoethyl nitrate by stirring with an excess of a thioacetate salt in the presence or absence of a crown ether catalyst in a methanolic solution at room temperature overnight. The product was isolated in 50% yield after silica gel flash chromatography.

The compound of formula 7 was synthesized from the dinitrate 10, by stirring of dinitrate 10 and a thiocyanate alkali metal salt (1 equivalent) in acetone at room temperature over a number of days. The white precipitate produced was removed by filtration and the filtrate concentrated and passed through a silica gel flash chromatography column, yielding the desired product as a colourless oil (50%) (Table 1).

The compound of formula 9 was synthesized from the dinitrate 10, by stirring of dinitrate 10 and a cyanide alkali metal salt in acetone at room temperature over a number of days, with or without the aid of phase transfer catalyst or crown ether. The precipitate was removed from the reaction mixture by filtration and the filtrate concentrated and passed through a silica gel flash chromatography column, yielding the desired product as a colourless oil: $^1$H NMR (CDCl$_3$) 5.30–5.43(1H, m), 4.82–4.90 (1H, dd), 4.65–4.75 (1H, dd), 3.85–3.97 (2H, dd).

aL, Can. J. Physiol. Pharmacol. (1989) 67, 403, incorporated herein by reference. Tissues were contracted submaximally with phenylephrine (0.1 μM) and exposed to various concentrations of nitrovasodilator to obtain concentration response curves. In this intact tissue assay, nitrates 2, 3, 4 and 5 were observed to cause relaxation of the tissue with a

TABLE 1

NMR, IR, m.p. and mass spec. characteristics of nitrates[a]

| m.p. | $^1$H-NMR(ppm)[b] | $^{13}$C-NMR(ppm)[b] | IR(cm$^{-1}$) | MS(m/z, intensity %) |
|---|---|---|---|---|
| 1 liquid | 5.43–5.55(2H, m), 4.84–4.93(2H, m), 4.60–4.69(2H, dd, J=6, 13Hz), 2.97–3.16(4H, m). | 77.08/77.00, 69.33/69.29, 37.05/36.89. | (neat), 1634, 1270, 1042, 995, 855. | (CI, Cl$^-$), 429(M+Cl, 100), 393(M-1, 10). |
| 2 86° C.(dec.) | (DMSO-d$_6$), 5.75–5.80(1H, m), 4.99–5.07(1H, dd, J=3, 13Hz), 4.77–4.86(1H, dd, J=6, 13 Hz), 3.20–3.23(2H, d, J=7 Hz) | (DMSO-d$_6$), 79.02, 70.97, 32.04. | (kBr), 1638, 1449, 1378, 1351, 1290, 1210, 1042, 654. | (ES$^+$, Na), 323(M+Na, 53). |
| 3 64–65° C. | 5.84–5.90(1H, m), 4.98–5.06(1H, dd, J=4, 12Hz), 4.77–4.83(1H, d, J=12Hz), 3.50–3.58(1H, dd, J=2, 15Hz), 3.31–3.42(1H, dd, J=7, 15Hz). | 80.49, 75.07, 64.04. | (kBr), 1649, 1339, 1287, 1122, 926. | (Cl, Cl$^-$), 202(M+Cl, 100) |
| 4 65–66° C. | 5.80–5.87(1H, m), 4.67–4.75(1H, dd, J=5, 11 Hz), 4.50–4.57(1H, dd, J=2, 11Hz), 3.69–3.80(1H, dd, J=8, 15Hz), 3.35–3.44(1H, dd, J=3, 15Hz). | 76.95, 69.88, 48.66. | (kBr), 1651, 1344, 1286, 1139, 937. | (Cl, Cl$^-$), 218(M+Cl, 100). |
| 6 liquid | 4.52–4.56(2H, t, J=6.5Hz), 3.16–3.20(2H, t, J=6.5Hz), 2.37(1H, s) | 70.8, 30.4, 26.0 | — | (Cl), 218(M+H, 23), 119(M-NO$_2$, 100). |
| 7 liquid | 5.45–5.55(1H, m), 4.87–4.95(1H, dd), 4.65–4.74(1H, dd), 3.18–3.38(2H, m) | 110.19, 76.40, 68.76, 32.09 | — | (Cl, Cl$^-$), 258(M+Cl, 100). |
| 8 164–165° C. | 4.77(2H, t, J=6Hz), 3.35(2H, t, J=6Hz) | — | — | (Cl), 218(M+H, 23), 119(M-NO$_2$, 100). |
| 10 liquid | 5.41–5.43(1H, m), 4.84–4.88(1H, dd, J=3, 13Hz), 4.68–4.73(1H, dd, J=6, 13Hz), 3.55–3.57(2H, dd, J=0.5, 6Hz) | 76.95, 69.16, 26.19 | (neat) 1647, 1428, 1288, 1271, 1010, 835 | — |

[a]All compounds were characterized by elemental analysis and/or high resolution mass spec., HPLC and NMR analysis for homogeneity.
[b]CDCl$_3$ was used as solvent for $^1$H-, $^{13}$C-NMR, unless otherwise indicated.

Figure 2:
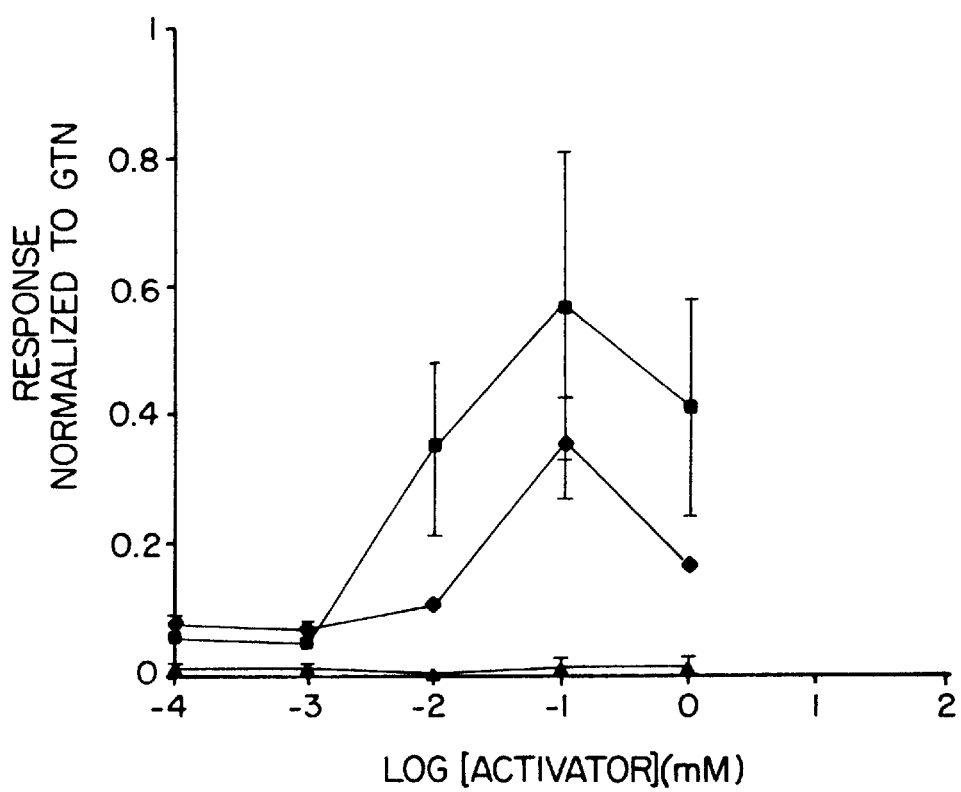
FIG. 2 is a graph showing the effect of compound 1; neat (triangles); with added L-cysteine (2 mM, diamonds); with added dithiothreitol (2 mM, DTT, squares); on soluble Gcase activity in the 105,000 g supernatant fraction of rat aorta homogenate, normalized to maximal GTN response carried out in identical Gcase preparations. Experimental incubations were performed at 37° C. for 10 min. Bars represent the mean ± standard errors calculated separately for each point.
Figure 3:
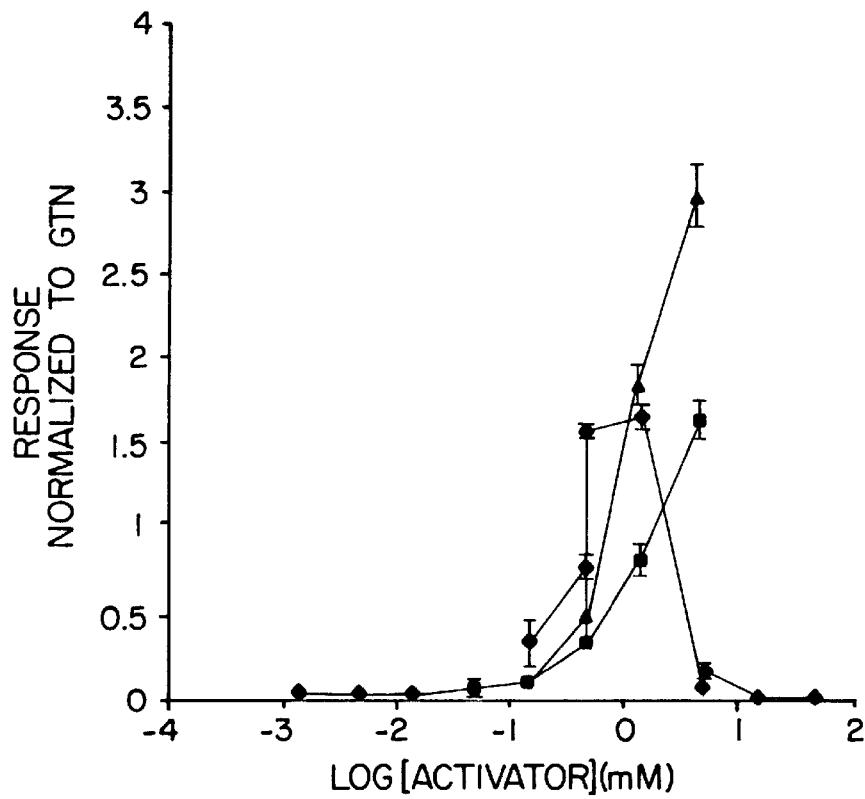
FIG. 3 is a graph showing the effect of compound 2; neat (diamonds); with added L-cysteine (2 mM, triangles); with added dithiothreitol (2 mM, DTT, squares); on soluble Gcase activity in the 105,000 g supernatant fraction of rat aorta homogenate, normalized to maximal GTN response carried out in identical Gcase preparations. Experimental incubations were performed at 37° C. for 10 min. Bars represent the mean ± standard errors calculated separately for each point.
Figure 4:
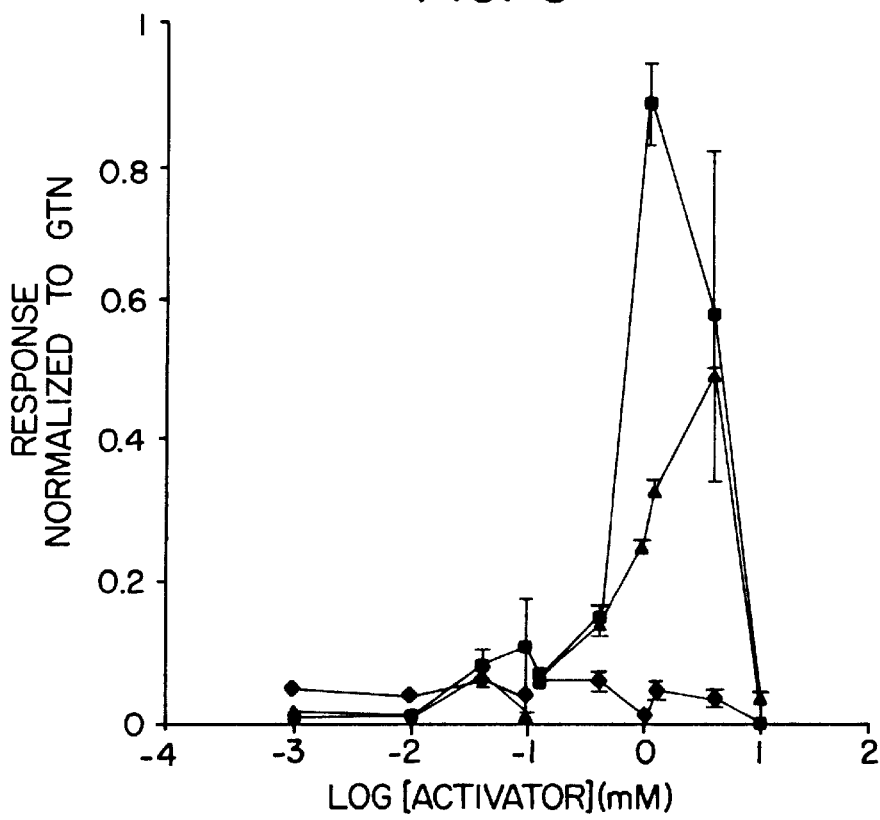
FIG. 4 is a graph showing the effect of compound 3; neat (diamonds); with added L-cysteine (2 mM, triangles); with added dithiothreitol (2 mM, DTF, squares); on soluble Gcase activity in the 105,000 g supernatant fraction of rat aorta homogenate, normalized to maximal GTN response carried out in identical Gcase preparations. Experimental incubations were performed at 37° C. for 10 min. Bars represent the mean ± standard errors calculated separately for each point.
Figure 5:
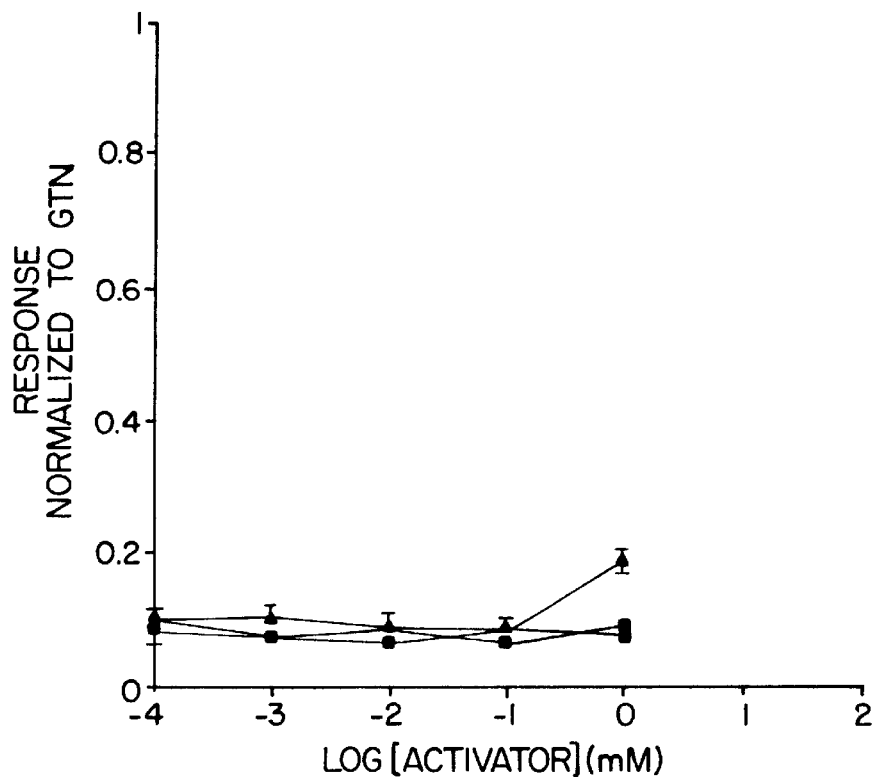
FIG. 5 is a graph showing the effect of compound 7; neat (diamonds); with added L-cysteine (2 mM, triangles); with added dithiothreitol (2 mM, DTT, squares); on soluble Gcase activity in the 105,000 g supernatant fraction of rat aorta homogenate, normalized to maximal GTN response carried out in identical Gcase preparations. Experimental incubations were performed at 37° C. for 10 min. Bars represent the mean ± standard errors calculated separately for each point.
Figure 6:
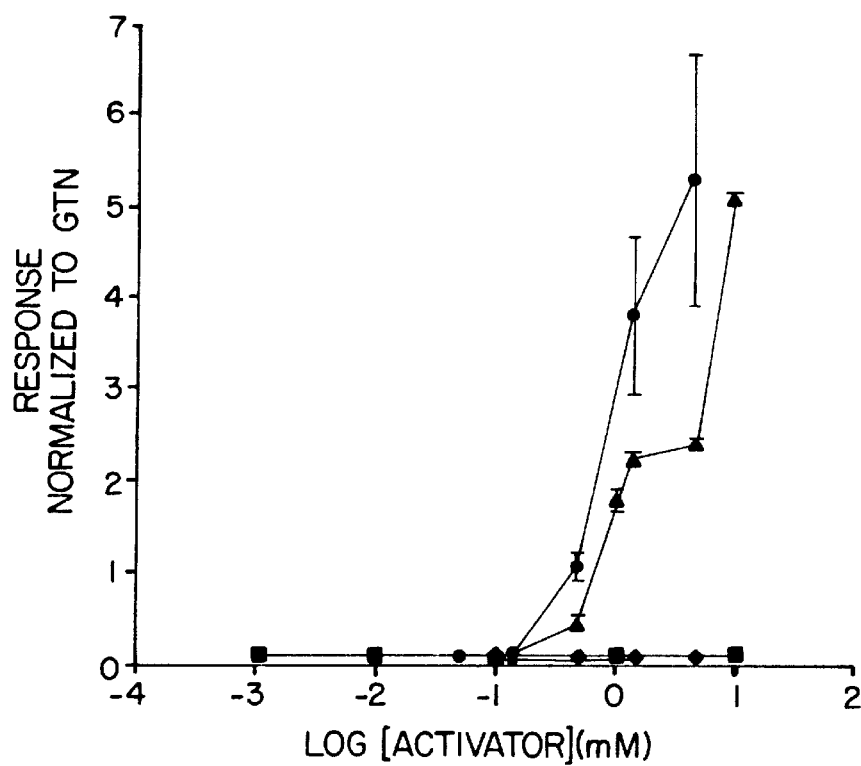
FIG. 6 is a graph showing the effect of compound 4; neat (diamonds); with added L-cysteine (2 mM, triangles; 5 mM, circles); with added dithiothreitol (2 mM, DTT, squares); on soluble Gcase activity in the 105,000 g supernatant fraction of rat aorta homogenate, normalized to maximal GTN response carried out in identical Gcase preparations. Experimental incubations were performed at 37° C. for 10 min. Bars represent the mean ± standard errors calculated separately for each point.
Figure 7:
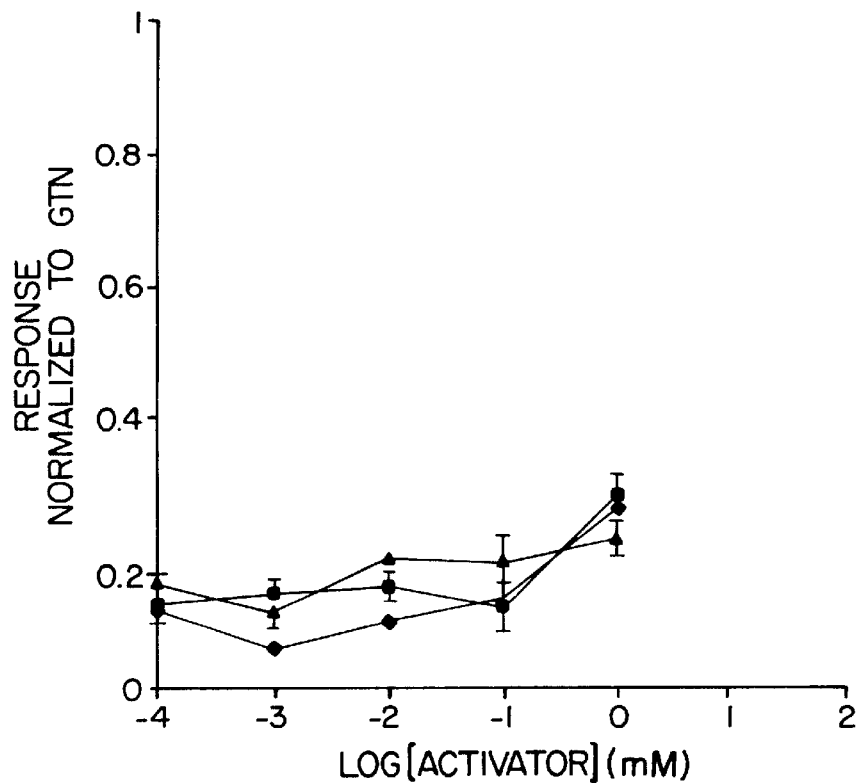
FIG. 7 is a graph showing the effect of compound 8; neat (diamonds); with added L-cysteine (2 mM, triangles); with added dithiothreitol (2 mM, DTT, squares); on soluble Gcase activity in the 105,000 g supernatant fraction of rat aorta homogenate, normalized to maximal GTN response carried out in identical Gcase preparations. Experimental incubations were performed at 37° C. for 10 min. Bars represent the mean ± standard errors calculated separately for each point.
Figure 8:
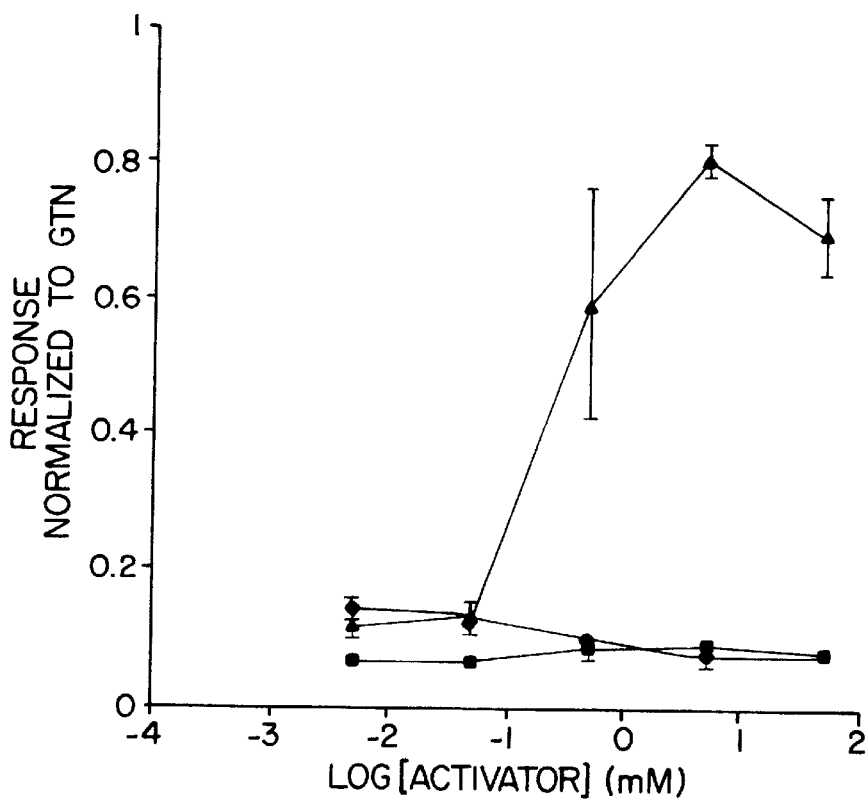
FIG. 8 is a graph showing the effect of compound 10; neat (diamonds); with added L-cysteine (2 mM, triangles); with added dithiothreitol (2 mM, DTT, squares); on soluble Gcase activity in the 105,000 g supernatant fraction of rat aorta homogenate, normalized to maximal GTN response carried out in identical Gcase preparations. Experimental incubations were performed at 37° C. for 10 min. Bars represent the mean ± standard errors calculated separately for each point.
Figure 9:
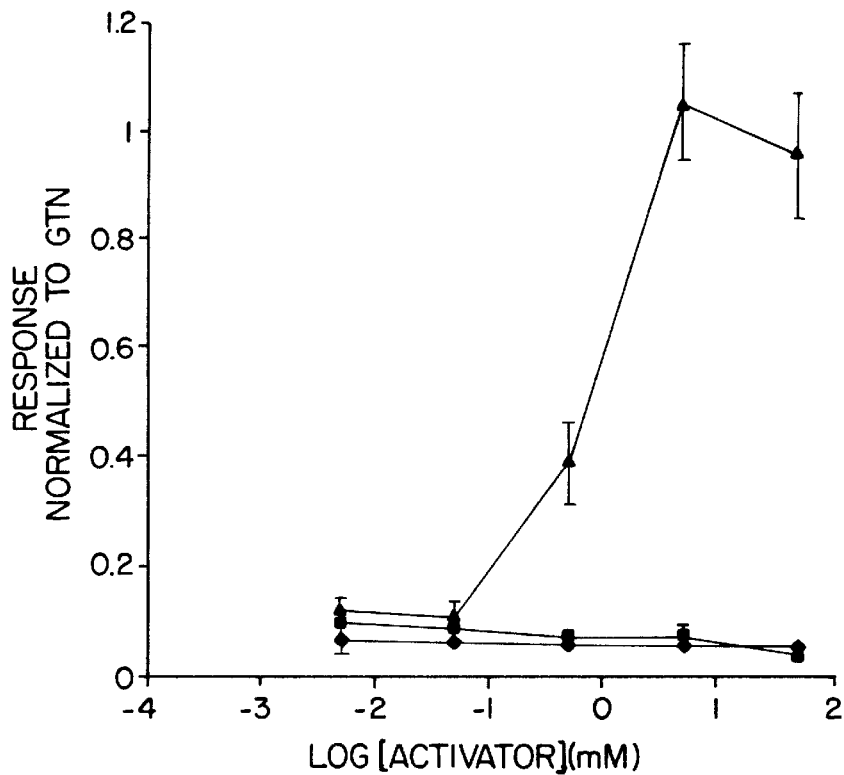
FIG. 9 is a graph showing the effect of compound 11; neat (diamonds); with added L-cysteine (2 mM, triangles); with added dithiothreitol (2 mM, DTT, squares); on soluble Gcase activity in the 105,000 g supernatant fraction of rat aorta homogenate, normalized to maximal GTN response carried out in identical Gcase preparations. Experimental incubations were performed at 37° C. for 10 min. Bars represent the mean ± standard errors calculated separately for each point.

Activation of soluble guanylyl cyclase (Gcase) by nitrates 1–5, 7 was assayed, employing partially purified enzyme freshly prepared from rat aorta homogenates, using the radioimmunoassay method described by Bennett et al., Can. J. Physiol. Pharmacol. (1992) 70, 1297, the disclosure of which is incorporated herein by reference. Dose-response curves were obtained for Gcase activation by nitrates 1–5, 7 and GTN in the presence and absence of cysteine and dithiothreitol (DTT; both 2 mM). The data from these curves are summarized in FIGS. 1–9, which give: concentrations of nitrates required to give a response equivalent to the maximal response seen for GTN+cysteine; the maximal response measured for each nitrate; and, where applicable, potency. The Gcase assay data show that dinitrate 2 activates Gcase, with a submillimolar EC-50 in the absence of any added thiol, in contrast to GTN which requires added cysteine (FIGS. 1, 3). Compounds 2 and 4 also activate Gcase in the presence of DTT in contrast to GTN (FIGS. 3, 6). Activation of Gcase by compound 5 was cysteine-dependent and the response was approximately one third of that observed with GTN. Activation of Gcase by compound 7 was cysteine-dependent and the response was very low (EC-50>1 mM) (FIG. 7). The activity of the tetranitrate 1 was again low and entirely equivalent to glycerol-1,2-dinitrate in this assay (FIG. 2). Relative to GTN itself, a wide range of potency is observed for the novel organic nitrate esters. No activation of Gcase by glycerol mononitrates is observed in this assay at the concentrations of nitrate employed.

Figure 10:
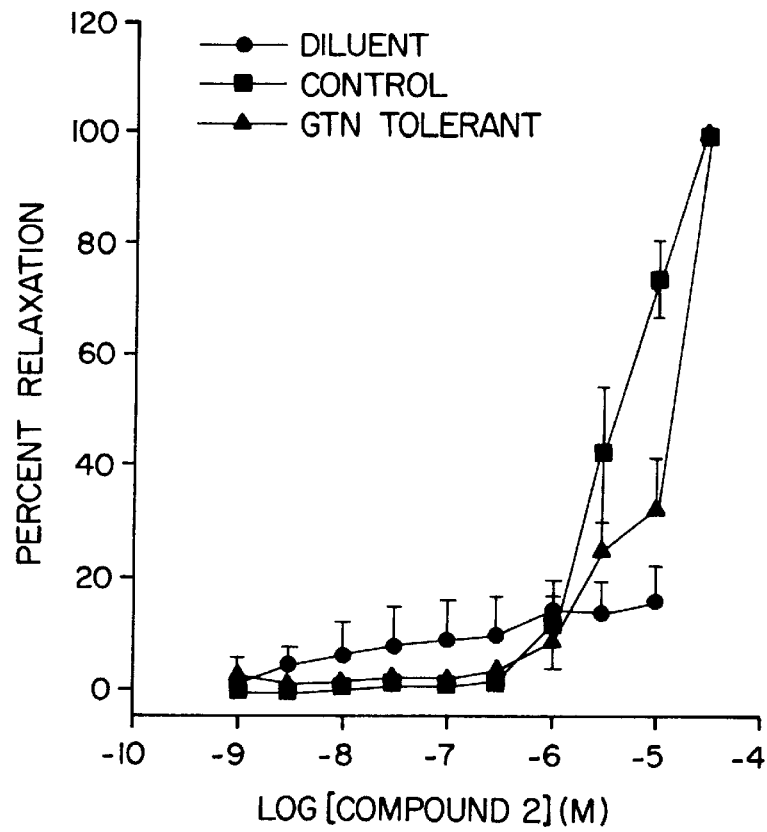
FIG. 10 is a graph showing the the relaxation induced by compound 2 in untreated and GTN tolerant rat aorta.
Figure 11A:
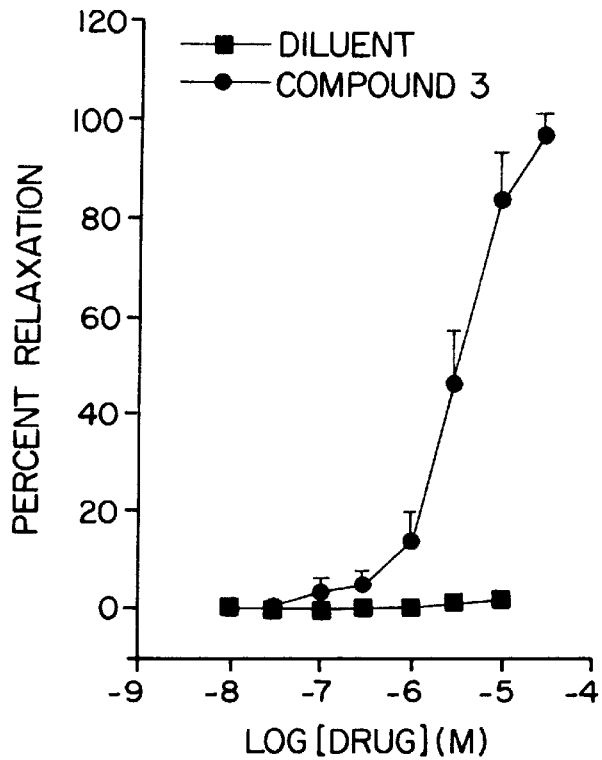
FIG. 11 is a graph showing the relaxation induced by compounds 3(a) and 4(b) in isolated rat aorta.
Figure 11B:
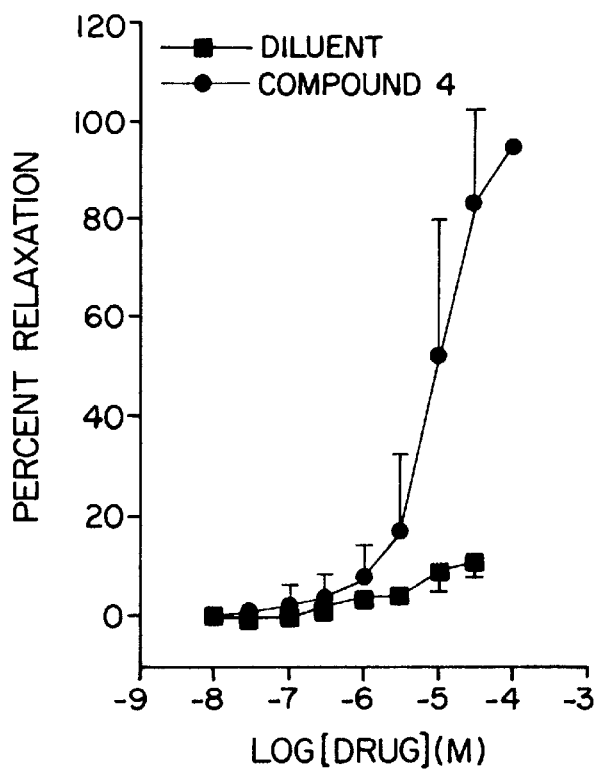
Figure 12:
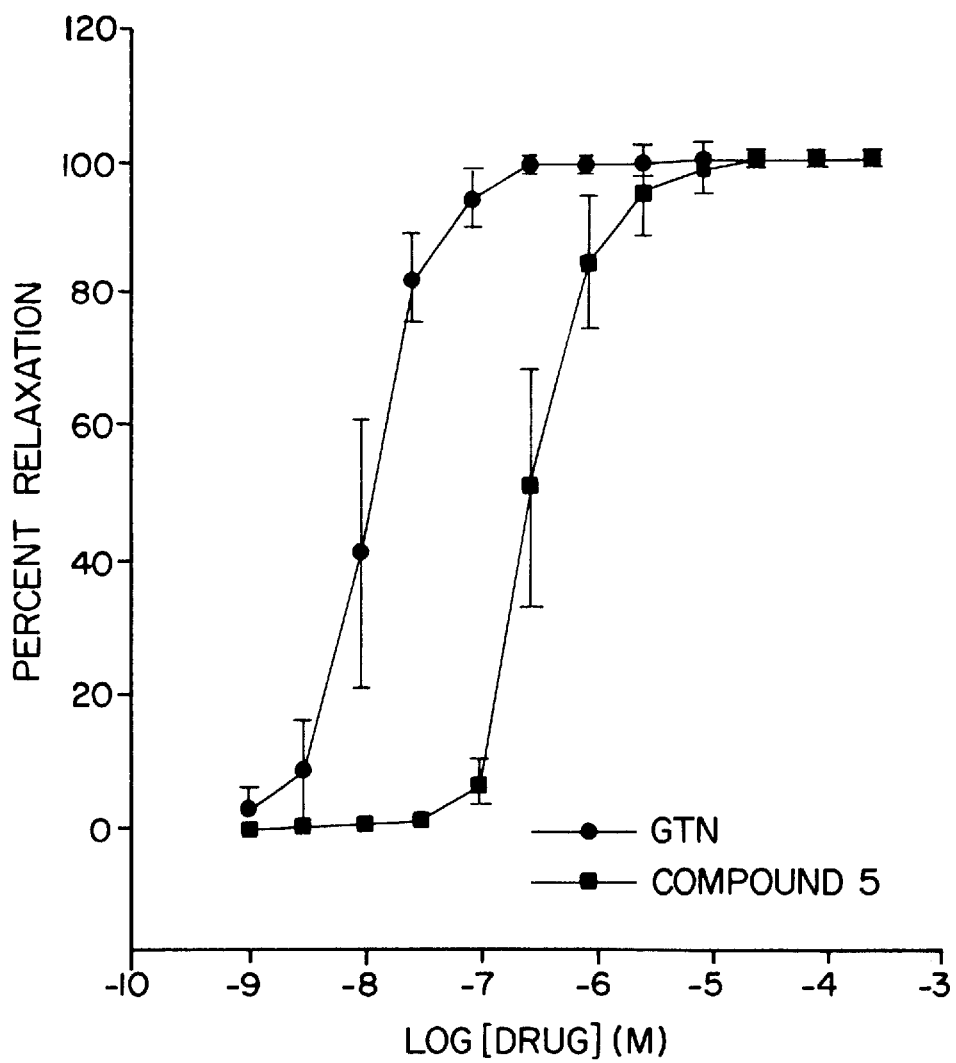
FIG. 12 is a graph showing the comparison of concentration response curves for GTN and compound 5 in isolated rat aorta. Data points represent mean ± SD (n=5–6).
Figure 13:
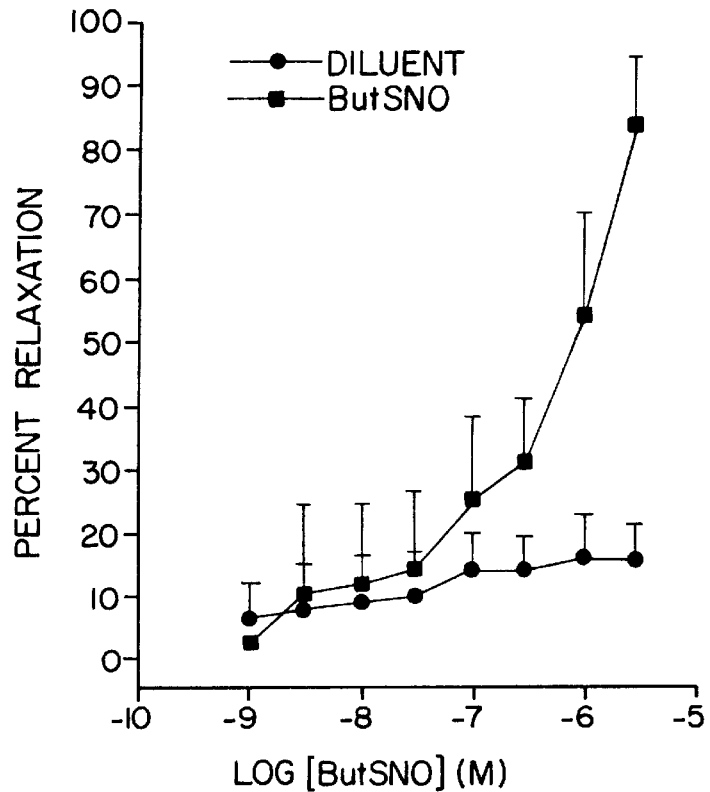
FIG. 13 is a graph showing the relaxation induced by tert-butyl nitrosothiol in isolated rat aorta.
Figure 14:
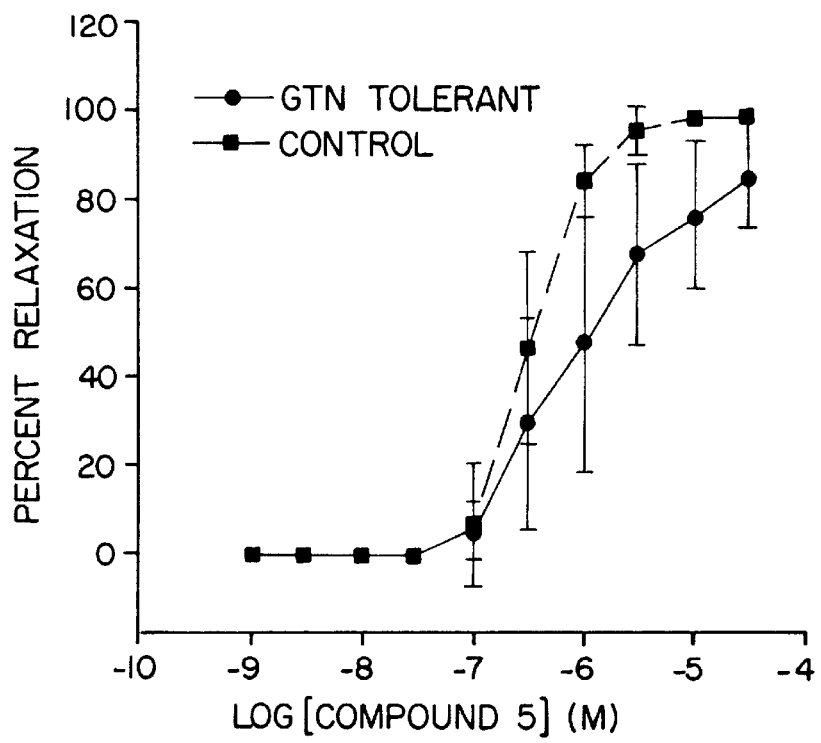
FIG. 14 is a graph showing the relaxation induced by compound 5 in untreated and GTN-tolerant isolated rat aorta.

In order to extend the Gcase data, the relaxing effects of nitrates 2, 3, 4 and 5 on rat aortic tissue were examined. Thoracic aortic strips were prepared from male Sprague-Dawley rats (Charles-River, Canada) as described in McGuire et al., J. Exp. Ther. (1994) 271, 708 and Stewart et maximal relaxant response equal to that obtained with GTN. However, the compounds differed in potency with EC-50 values of 3.9 μM (FIG. 10), 3.4 μM (FIG. 11), 9.1 μM (FIG. 11) and 0.2 μM (FIG. 12) for compounds 2, 3, 4 and 5 respectively. The EC-50 values for a nitrosothiol (tert-butyl nitrosothiol, FIG. 13) and for GTN itself (FIG. 12) were 11.2 μM and 14 nM, respectively. Compounds 2 and 5 were tested for their ability to cause vascular relaxation in tissues that had been made tolerant to the relaxant effect of GTN. GTN tolerance was induced by incubating tissues with high concentrations of GTN (0.5 mM GTN for 30 min). Under these conditions, the maximal relaxant effect of compounds 2 (FIG. 10) and 5 (FIG. 14) was not significantly different from that of untreated tissue. The EC-50 for relaxation was increased approximately threefold, but the difference was not statistically significant.

Figure 15:
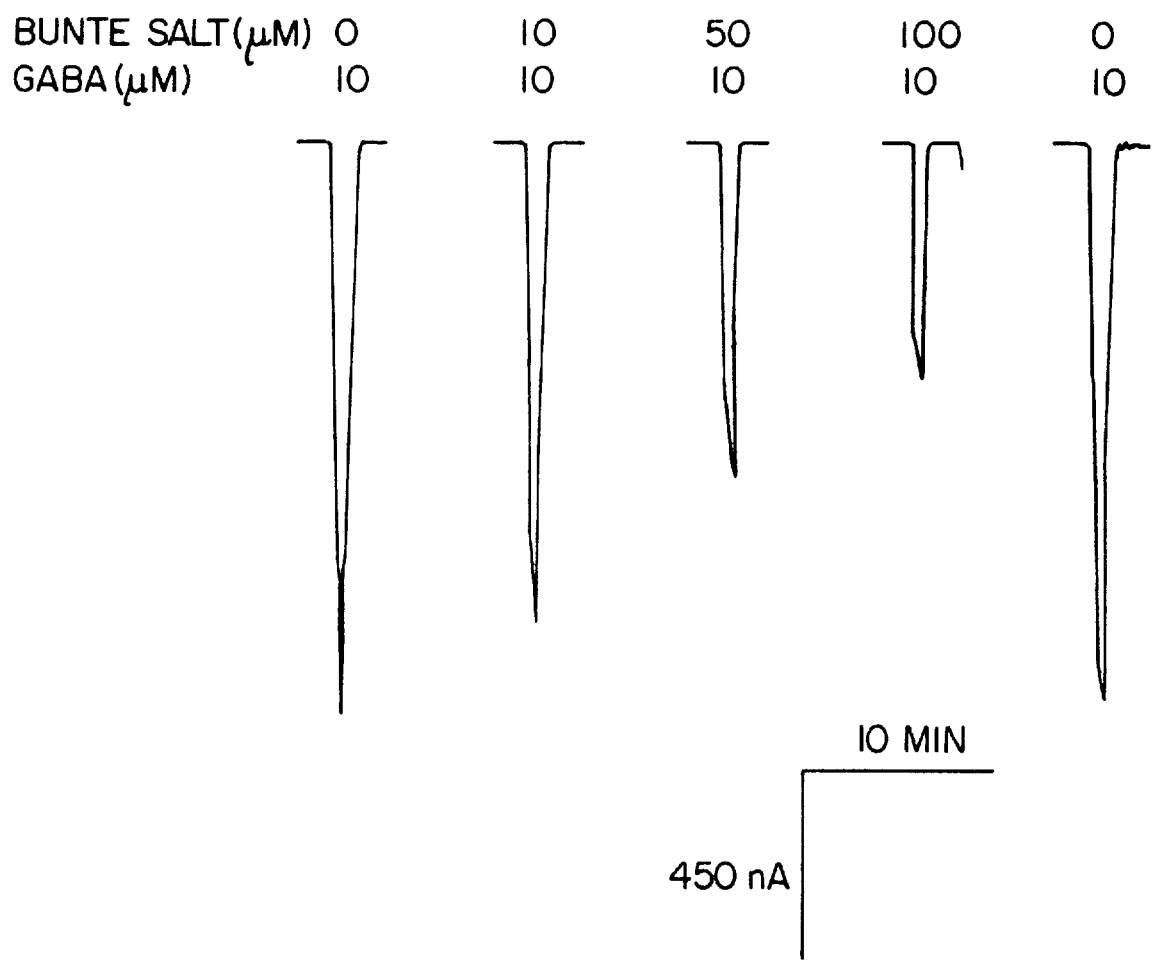
FIG. 15 is a graph showing the $GABA_A$ receptor-activated membrane current recorded in an oocyte expressing the $\alpha1\beta2\gamma2L$ receptor isoform. GABA (10 $\mu$M) was applied until the peak steady-state current response was obtained. Compound 2 (Bunte salt, 10–100 $\mu$M) was pre-applied for 30 seconds prior to exposure of the oocyte to GABA. At 100 $\mu$M the Bunte salt produced a 55% inhibition of the response to 10 $\mu$M GABA. Similar results were obtained in 5 different oocytes.
Figure 16:
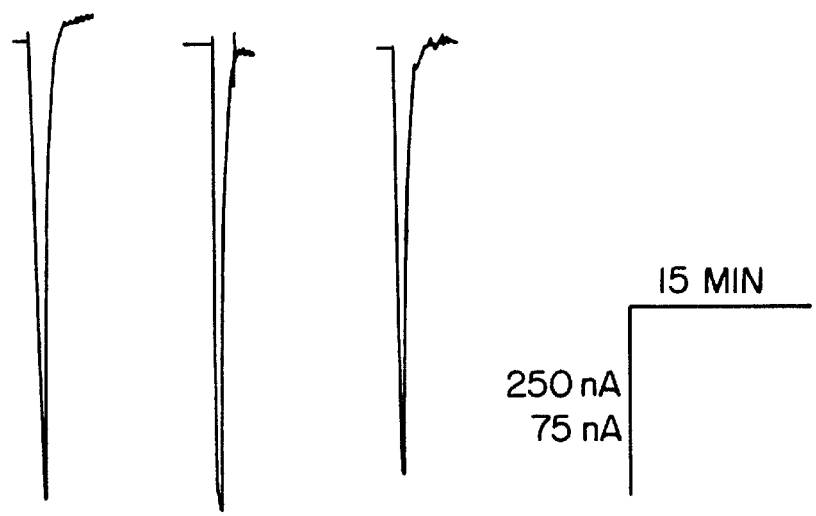
FIG. 16 is a graph showing that nitric oxide donors have no effect on $GABA_A$ receptors expressed in Xenopus oocytes. Diethylamine nonoate salt (DEA) and t-butylnitrosothiol (t-BuSNO) which both spontaneously release nitric oxide in aqueous solution, had no effect on $GABA_A$ receptor-activated membrane current in an oocyte expressing the $\alpha1\beta2\gamma2L$ receptor isoform. In contrast, nitroglycerin (GTN) produced a reversible inhibition of the GABA response.
Figure 16:
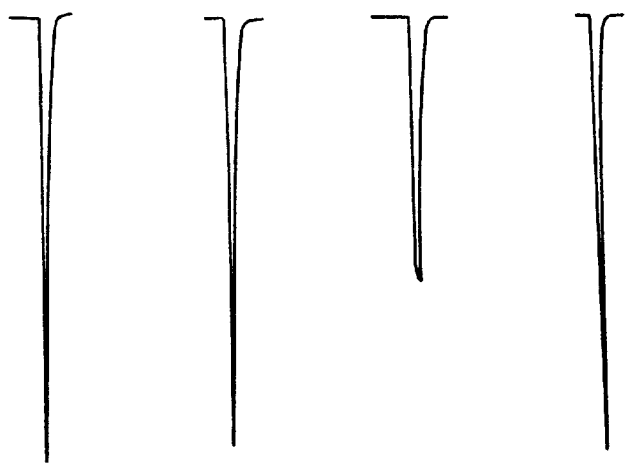
Figure 17:
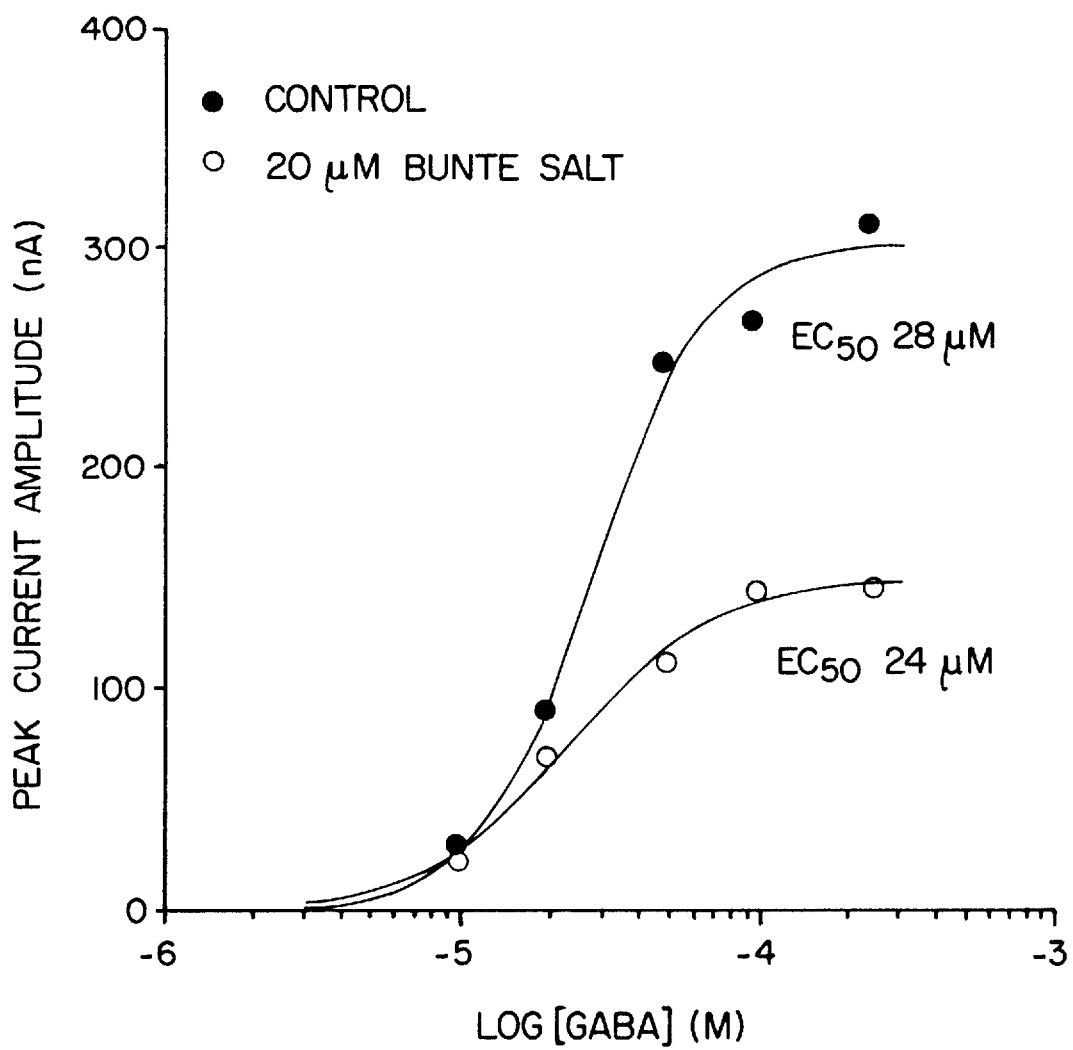
FIG. 17 is a graph showing that the concentration response relationship for activation of the $GABA_A$ receptor is altered in a non-competitive manner by organic nitrate esters. The Bunte salt 2 (pre-applied for 30 seconds) decreased the peak current amplitude from 302 nA to 150 nA. However, the $EC_{50}$ concentration (GABA concentration producing 50% of the maximal response) for GABA was not changed. This suggests that organic nitrates produce an allosteric alteration in $GABA_A$ receptor activation.

The direct effects of organic nitrates on amino acid neurotransmitter receptors has been tested using the Xenopus oocyte expression system and two-electrode voltage-clamp recording methods. Human recombinant γ-aminobutyric acid type A (GABA$_A$) receptors composed of α1β2γ2L subunits were expressed in Xenopus oocytes as described in Reynolds and Maitra, Eur. J. Pharmacol. (1996) 314, 151–156, incorporated herein by reference. GABA$_A$ receptor-activated membrane current was recorded in individual oocytes, and modulation of this current by GTN and nitrate esters described in this application was assessed. GTN and the Bunte salt, compound 2, were found to inhibit GABA$_A$ receptor-activated membrane current with similar potencies. Concentrations of 10–100 μM of the nitrates produced a concentration-dependent inhibition of the GABA response (FIG. 15). This effect appears to be unrelated to the production or release of nitric oxide, as nitric oxide generating compounds do not mimic this effect of GTN or the Bunte salt 2 to inhibit $GABA_A$ receptor function (FIG. 16). Organic nitrates such as GTN and the Bunte salt 2 do not compete with GABA for binding to the $GABA_A$ receptor. Rather, they produce an allosteric modulation of the receptor that decreases the maximal current without changing the apparent affinity of the receptor for GABA (FIG. 17). Other organic nitrates described in this application have been found to have similar inhibitory effects on $GABA_A$ receptor-activated membrane current. In behavioural models of learning and memory, drugs which decrease $GABA_A$ receptor function improve performance on learning and memory tasks (Venault, P. G., Chapouthier, L., Prado de Carvalho and Rossier, J., *Encephale*, (1992) 18, 655). Thus, the behavioural effect of organic nitrates, developed to act as modulators of $GABA_A$ receptor function, will be to improve memory performance and cognition in patient populations. It will be appreciated, therefore, that these nitrate esters can be used for treatment of: stroke; dementias of all type; trauma; drug-induced brain damage; and aging.

Figure 18:
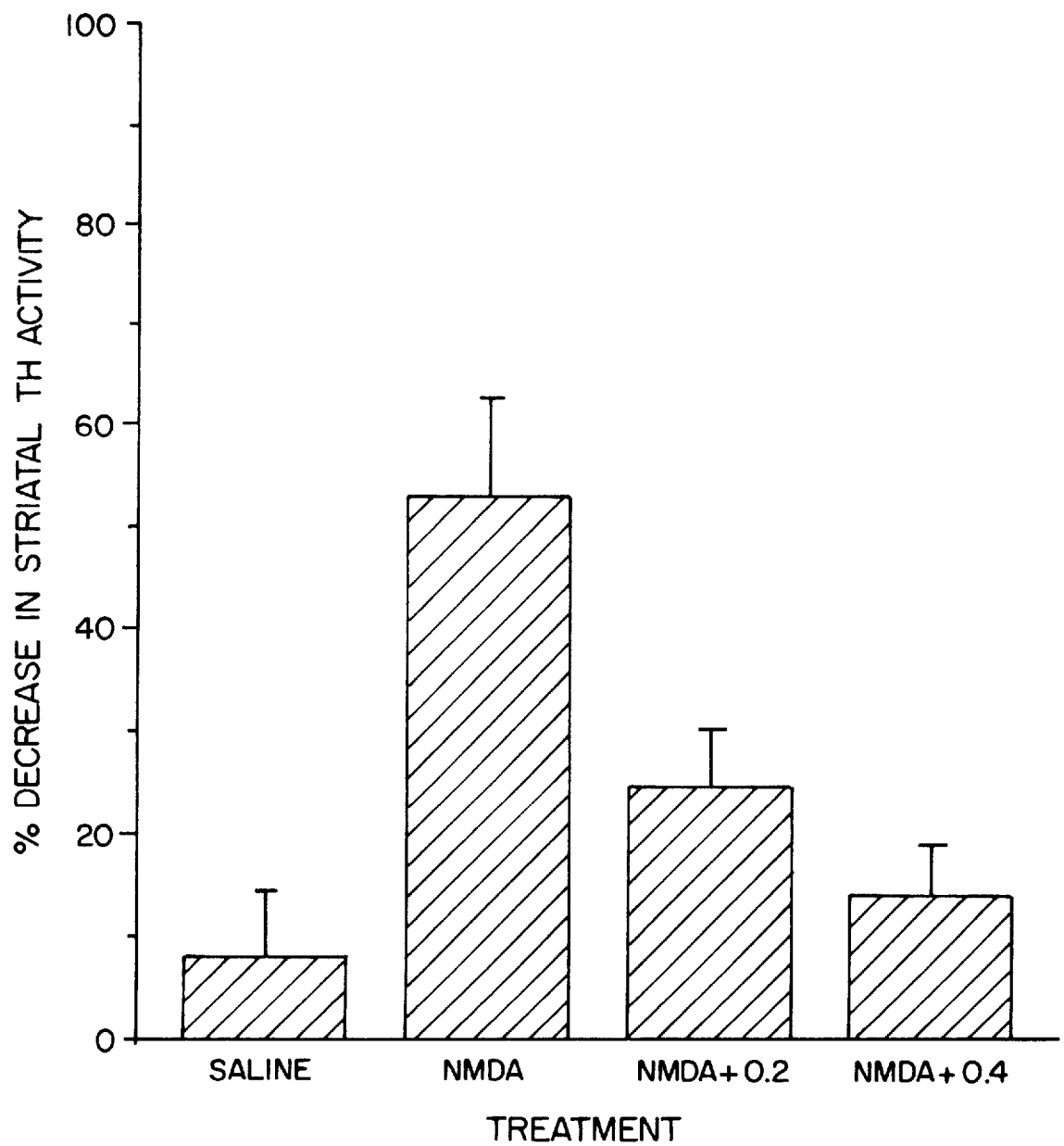
FIG. 18 is a graph showing the effect of GTN (0.2 or 0.4 mg/hr) implanted subcutaneously one hour prior to an infusion of NMDA into the substantia nigra on striatal tyrosine hydroxylase (TH) activity.
Figure 19:
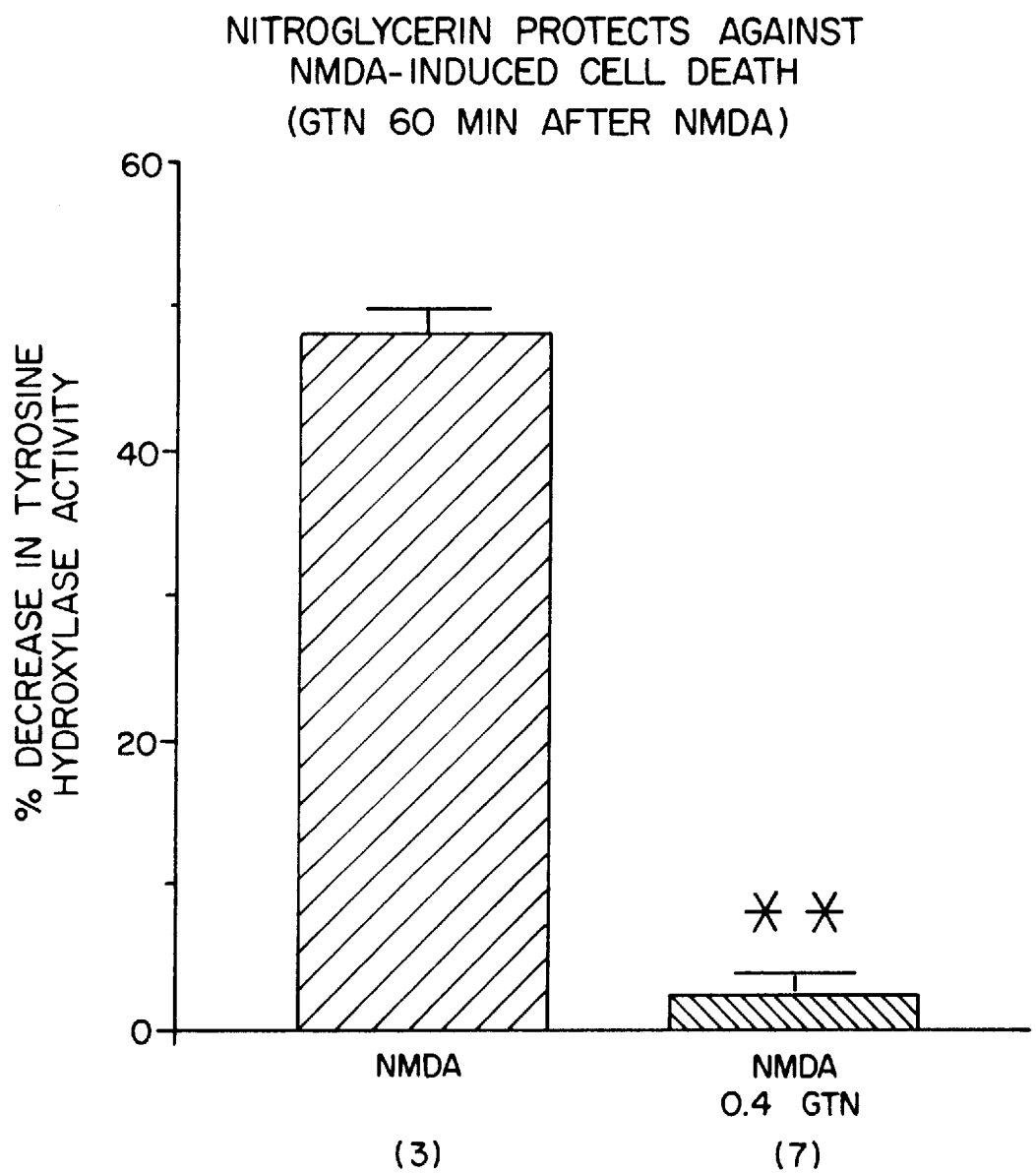
FIG. 19 is a graph showing the effect of GTN (0.4 mg/hr) implanted subcutaneously one hour after an infusion of NMDA into the substantia nigra on striatal (TH) activity.
Figure 20:
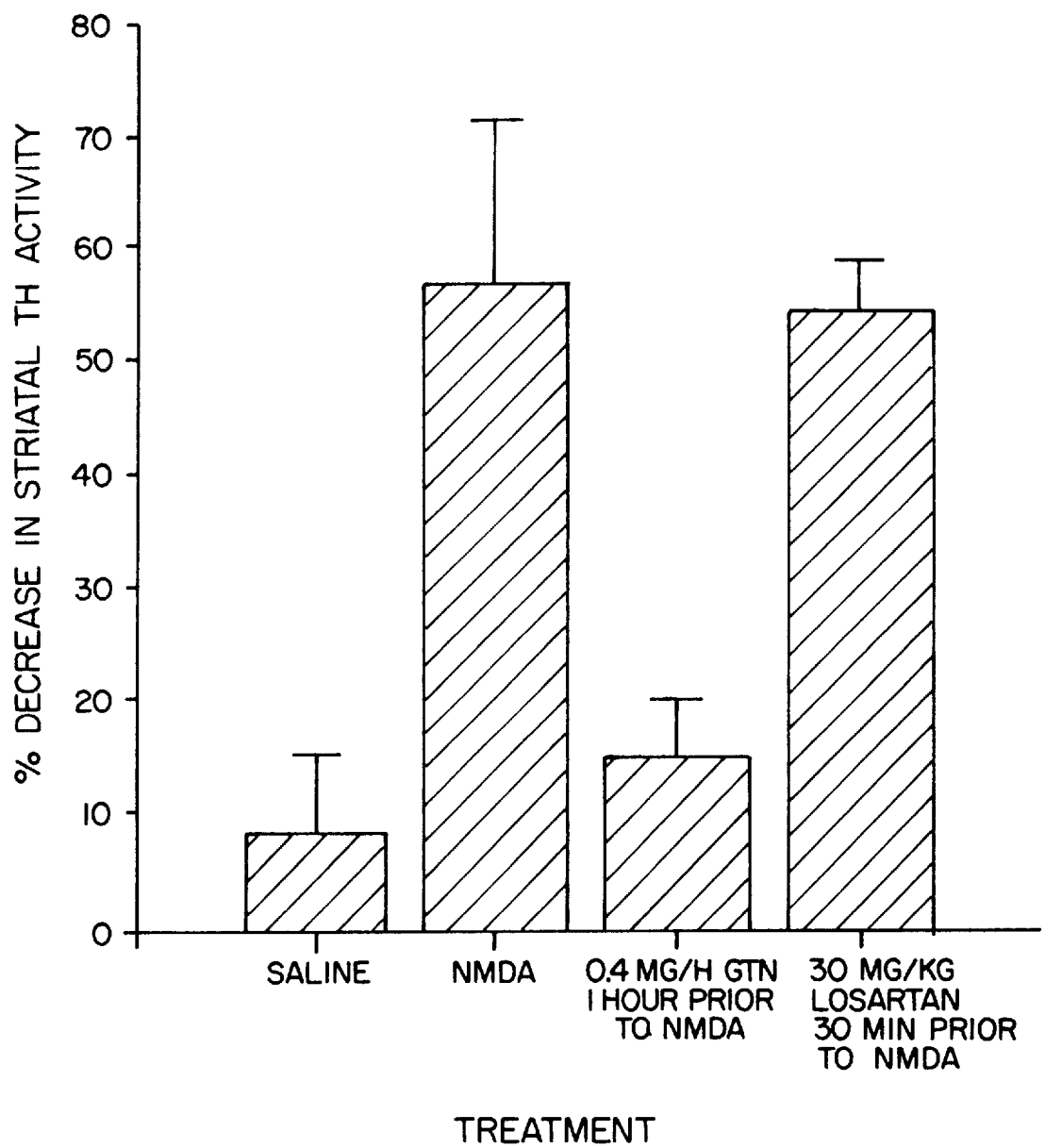
FIG. 20 is a graph showing the percent decrease in striatal TH activity. Male Sprague-Dawley rats were stereotactically infused with NMDA into the substantia nigra and the striata were dissected and assayed for TH activity. The striata of each animal were compared to express neurotoxicity as a percent decrease in TH activity of the ipsilateral striatum as compared to the contralateral striatum. Animals pretreated with GTN showed significant amounts of neuroprotection; whereas, animals pretreated with losartan did not show any evidence of neuroprotection.
Figure 21A:
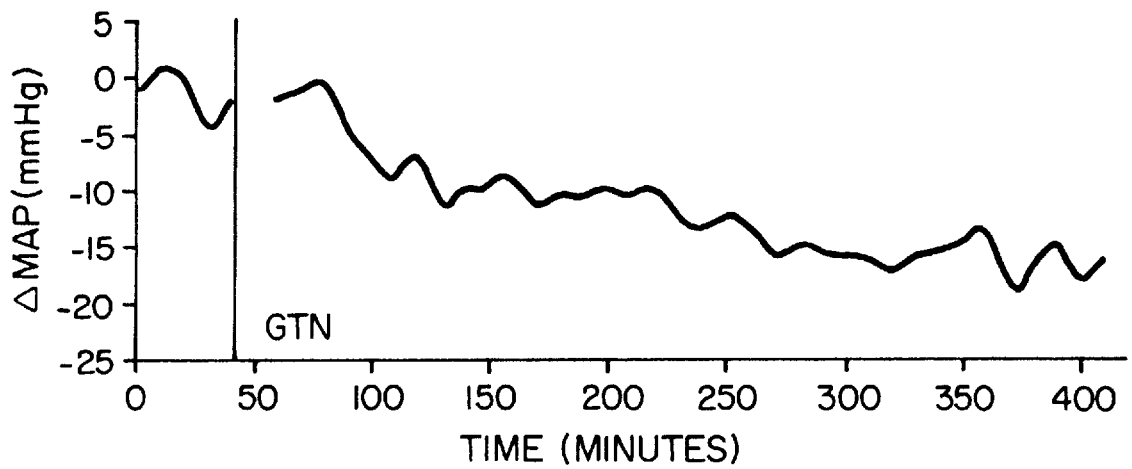
FIGS. 21(a) and (b) are graphs showing the blood pressure profiles. Male Sprague-Dawley rats with aortic catheters were connected to pressure transducers which recorded blood pressure for 4 to 8 hours. Mean arterial pressure (MAP) curves for typical animals are represented above. (a) The animals treated with transdermal 0.4 mg/hour GTN patches implanted in the dorsal neck region, showed a 15% decrease in MAP 250 minutes post-implantation. (b) Animals treated with a single 30 mg/kg intraperitoneal injection of losartan showed a 20% decrease in MAP 250 minutes after injection. From these data, treatment protocols for the NMDA infusion experiments were generated.
Figure 21B:
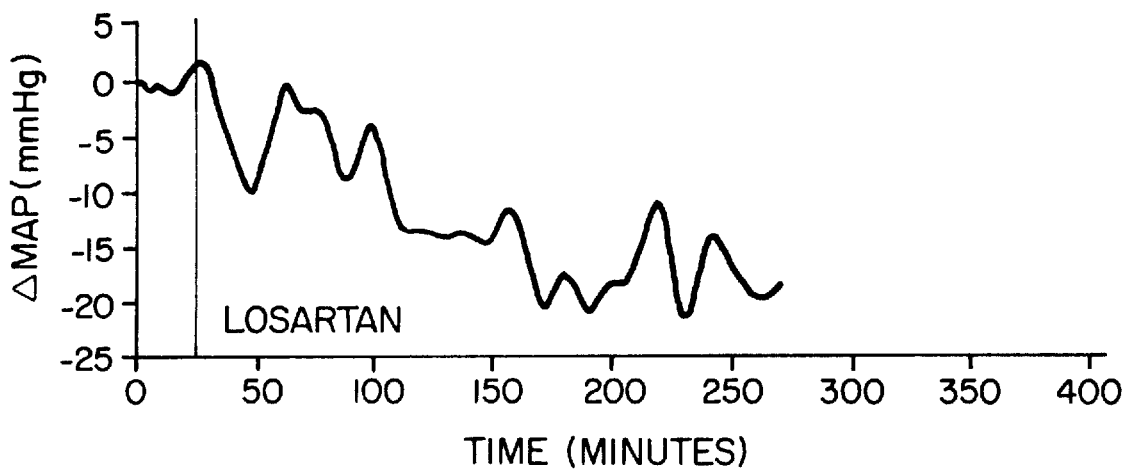

GTN, owing to its structural properties, is capable of preventing damage or loss of neurons induced by an excitotoxic insult involving excessive activation of glutamate receptors on brain neurons. The neuroprotective action of GTN on the nigrostriatal dopamine neurons of the rat was examined in a model of dopaminergic neuron excitotoxicity using a previously described method: Connop et aL, *Brain Research* (1995) 676, 124–132, incorporated herein by reference. An infusion of 15 nmoles of the glutamate receptor agonist N-Methyl-D-Aspartate (NMDA) into the right substantia nigra of adult rats (300–325 g) was made. A subdermal patch containing GTN (to release GTN at the rate of 0.2 or 0.4 mg/hr) was implanted under the skin in the dorsal neck either before or one hour after the focal infusion of NMDA (FIG. 19). In separate experiments, losartan, a vasodilator drug that acts by blocking angiotensin II type I receptors, replaced the administration of GTN prior to NMDA infusion. The blood pressure of treated animals was monitored. Four days after the NMDA injection, activity of tyrosine hydroxylase (TH), a marker for dopamine neurons, was measured in the striatum on injected and uninjected sides of the brain. In the absence of GTN, injection of NMDA produced 53% decrease in ipsilateral striatal TH activity, indicating a significant depletion of dopaminergic neurons projecting to the striatum (FIG. 18). Treatment with NMDA coupled to 0.2 and 0.4 mg/hr GTN resulted in 25% and 18% decrease in striatal TH activity, respectively (FIG. 18). In animals treated with GTN (0.4 mg/hr) 1 hour after the NMDA infusion, the decrease in striatal TH was 15% (FIG. 19). Comparison of these values with those obtained in the absence of GTN treatment revealed a significantly lower depletion of dopaminergic neurons following treatment with GTN. The data showed that GTN significantly reduces NMDA-induced excitotoxic damage to dopaminergic neurons. In the losartan-treated (30 mg/kg) animal the decrease in TH activity was 53%. This value was not different from that obtained in the NMDA-injected animals. The data indicated that losartan does not inhibit NMDA-induced dopaminergic neuron damage. In the blood pressure experiments, GTN (0.4 mg/hr) treatment resulted in a 15% decrease in the mean arterial pressure (MAP) and losartan (30 mg/kg) treatment resulted in a 20% decrease in the MAP (FIG. 20). The results of blood pressure and toxicity experiments show that the ability of GTN to decrease NMDA-induced dopaminergic neuron damage is not related to decreases in blood pressure, since both GTN and losartan decreased blood pressure but only GTN produced neuroprotection. It will be appreciated, therefore, that these nitrate esters can be used for treatment of: stroke; Parkinson's disease; Alzheimer's disease; Huntington's disease; multiple sclerosis; amyotrophic lateral sclerosis; AIDS-induced dementia; epilepsy; alcoholism; alcohol withdrawal; drug-induced seizures; viral/bacterial/fever-induced seizures; trauma to the head; hypoglycemia; hypoxia; myocardial infarction; cerebral vascular occlusion; cerebral vascular hemorrhage; hemorrhage; environmental excitoxins of plant, animal and marine origin.

It will be appreciated by those skilled in the art, that any nitrate ester in which vasodilatory potency is reduced and neuroprotective potency increased, represents a new and useful therapeutic agent for use in neuroprotection, including in treatment of stroke; Parkinson's disease; Alzheimer's disease; Huntington's disease; multiple sclerosis; amyotrophic lateral sclerosis; AIDS-induced dementia; epilepsy; alcoholism; alcohol withdrawal; drug-induced seizures; viral/bacterial/fever-induced seizures; trauma to the head; hypoglycemia; hypoxia; myocardial infarction; cerebral vascular occlusion; cerebral vascular hemorrhage; hemorrhage; environmental excitoxins of plant, animal and marine origin. GTN itself, proposed as a neuroprotective agent, has no clinical utility as a neuroprotective agent in therapy owing to its extraordinarily high vasodilatory potency.

It will be appreciated, additionally, by those skilled in the art, that the use in therapy of any nitrate ester in cognition enhancment, represents a new and useful therapeutic treatment for cognition enhancement, including in treatment of: stroke; dementias of all type, trauma, drug-induced brain damage, and aging.

A composition of the invention for therapeutic use comprises a nitrate ester and a physiologically acceptable carrier therefor. The term "physiologically acceptable carrier" as used herein includes diluents, solvents or dispersion media such as, for example, water, saline, glycerol and the like, as well other carriers, such as, for example, liposomes. Liposomes include water-in-oil-in-water emulsions as well as conventional liposomes (Strejan et al. (1984) *J. Neuroimmunol* 7, 27). A composition of the invention may be co-administered to a subject in need thereof with agent(s) to prevent its inactivation by enzymes, acids or other natural conditions. Such agents include coatings, enzyme inhibitors and the like. A composition of the invention may include agent(s) to facilitate delivery of the active compound, or which delay absorption, such as, for example, gelatin. A composition of the invention may also include antibacterial or antifungal agents, such as, for example, thimersol, parabens or the like. The use of such media and agents for pharmaceutically active substances is well known in the art. Except insofar as any conventional medium or agent is incompatible with the active compound, its use in the therapeutic compositions of the invention is contemplated.

Methods of the invention provide administration of an active compound (nitrate ester or salt thereof) to a subject in need thereof in a biologically compatible form. That is, the active compound is administered in a form in which any toxic effects are outweighed by the therapeutic effects of the active compound. Administration of a therapeutically active amount of a composition of the present invention means an amount effective, at dosages and for periods of time necessary, to achieve the desired result. A therapeutically active amount of nitrate esters of the invention may vary according to factors such as the disease state, age, sex, and weight of the individual, and the ability of the nitrate esters to elicit a desired response in the individual.

The active compound (nitrate ester or salt thereof) may be administered in any convenient manner, such as, for example, by injection (subcutaneous, intravenous, intraventricular, intrathecally, intramuscular, intracavernous, etc.), oral administration, inhalation, transdermal application, lingual, sublingual, buccal, nasal, or rectal administration. The active compound may also be administered parenterally or intraperitoneally. In certain preferred embodiments of the invention, transdermal patches (containing from about 0.05 mg to about 1 g per single dosage form) and ointments or creams are suitable for transdermal and topical administration.

Although this invention is described in detail with reference to preferred embodiments thereof, these embodiments are offered to illustrate but not to limit the invention. It is possible to make other embodiments that employ the principles of the invention and that fall within its spirit and scope as defined by the claims appended hereto.

We claim:

1. An aliphatic nitrate ester or salt thereof, containing at least one nitrate group, in which a S or P atom is situated β or γ to a nitrate group, or their congener, having a general formula:

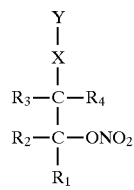

where X is CN, NHOH, $N_2H_3$, $N_2H_2R_{13}$, $N_2HR_{13}R_{14}$, $N_3$, SCN, $SCN_2H_2(R_5)_2$, $SCN_2H_3(R_5)$, $SC(O)N(R_5)_2$, $SC(O)NHR_5$, $CO_2M$, $CO_2H$, $CO_2R_{11}$, $C(O)$, $C(O)R_{12}$, $C(O)(OR_{13})$, $PO_2M$, $P(O)(OR_{14})$, $P(O)(R_{13})$, SO, $SO_2$, $C(O)(SR_{13})$, or $SSR_4$;

Y is SCN, $SCN_2H_2(R_5)_2$, $SC(O)NHR_5$, $SC(O)N(R_5)_2$, $SR_4$, $SR_{10}$, $SSR_{10}$, $SO_2M$, $SO_3M$, $PO_3HM$, $PO_3M_2$, $P(O)(OR_5)(OR_6)$, or $P(O)(OR_6)(OM)$, CN, $N_3$, $N_2H_2R_{13}$, $N_2HR_{13}R_{14}$, $CO_2M$, $CO_2H$, $CO_2R_{11}$, $C(O)R_{12}$, $C(O)(SR_{13})$, or does not exist;

$R_5$, $R_6$, $R_8$, $R_9$, $R_{10}$, $R_{12}$, $R_{13}$, $R_{14}$, $R_{15}$, $R_{16}$, are the same or different alkyls containing 1–12 carbon atoms which may contain 1–4 $ONO_2$ substituents or $C_1$ or $C_2$ connections to $R_1$–$R_3$ in cyclic derivatives;

$R_7$, $R_{11}$, are $C_1$–$C_8$ alkyl or acyl;

$R_2$ and $R_4$ are the same or different and selected from H, $ONO_2$, $C_1$–$C_4$ alkyl optionally bearing 1–3 nitrate groups, and acyl groups (—$C(O)R_{10}$);

$R_1$ and $R_3$ are the same or different and selected from H, $C_1$–$C_4$ alkyl and chains, which may include one O, linking $R_1$ and $R_3$ to form pentosyl, hexosyl, cyclopentyl or cycohexyl rings, which rings optionally bear hydroxyl substituents; and M is H, $Na^+$, $K^+$, $NH_4^+$ or $N^+H_nR_{11(4-n)}$ where n is 0–3; and with the proviso that, when $R_5$ is an alkyl group, and $R_1$ $R_2$ and $R_4$ are H, $R_3$ is not H or methyl.

2. The aliphatic nitrate ester or salt thereof of claim 1, where X is $C(O)$, $PO_2M$, $P(O)(OR_{14})$, $P(O)R_{13}$, SO, or $SO_2$.

3. The aliphatic nitrate ester or salt thereof of claim 1, where X is CN, NHOH, $N_2H_3$, $N_2H_2R_{13}$, $N_2HR_{13}R_{14}$, $N_3$, SCN, $SCN_2H_2(R_5)_2$, $SCN_2H_3(R_5)$, $SC(O)N(R_5)_2$, $SC(O)NHR_5$, $CO_2M$, $CO_2H$, $CO_2R_{11}$, $C(O)R_{12}$, $C(O)(OR_{13})$, $SR_4$, $C(O)(SR_{13})$, or $SSR_4$; and where Y does not exist.

4. An aliphatic nitrate ester having a formula selected from the group consisting of:

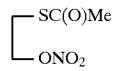

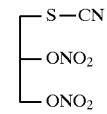

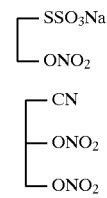

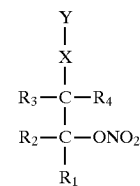

5. A pharmaceutical composition comprising an effective amount of an aliphatic nitrate ester or a pharmaceutically acceptable salt thereof, having the formula:

$$\begin{array}{c} Y \\ | \\ X \\ | \\ R_3-C-R_4 \\ | \\ R_2-C-ONO_2 \\ | \\ R_1 \end{array}$$

where X is CN, NHOH, $N_2H_3$, $N_2H_2R_{13}$, $N_2HR_{13}R_{14}$, $N_3$, SCN, $SCN_2H_2(R_5)_2$, $SCN_2H_3(R_5)$, $SC(O)N(R_5)_2$, $SC(O)NHR_5$, $CO_2M$, $CO_2H$, $CO_2R_{11}$, $C(O)$, $C(O)R_{12}$, $C(O)(OR_{13})$, $PO_2M$, $P(O)(OR_{14})$, $P(O)(R_{13})$, SO, $SO_2$, $C(O)(SR_{13})$, or $SSR_4$;

Y is SCN, $SCN_2H_2(R_5)_2$, $SC(O)NHR_5$, $SC(O)N(R_5)_2$, $SR_4$, $SR_{10}$, $SSR_{10}$, $SO_2M$, $SO_3M$, $PO_3HM$, $PO_3M_2$, $P(O)(OR_5)(OR_6)$, or $P(O)(OR_6)(OM)$, CN, $N_3$, $N_2H_2R_{13}$, $N_2HR_{13}R_{14}$, $CO_2M$, $CO_2H$, $CO_2R_{11}$, $C(O)R_{12}$, $C(O)(SR_{13})$, or does not exist;

$R_5$, $R_6$, $R_8$, $R_9$, $R_{10}$, $R_{12}$, $R_{13}$, $R_{14}$, $R_{15}$, $R_{16}$, are the same or different alkyls containing 1–12 carbon atoms which may contain 1–4 $ONO_2$ substituents or $C_1$ or $C_2$ connections to $R_1$–$R_3$, in cyclic derivatives;

$R_7$, $R_{11}$ are $C_1$–$C_8$, alkyl or acyl, $R_2$ and $R_4$ are the same or different and selected from H, $ONO_2$, $C_1$–$C_4$ alkyl optionally bearing 1–3 nitrate groups, and acyl groups (—$C(O)R_{10}$);

$R_1$ and $R_3$ are the same or different and selected from H, $C_1$–$C_4$ alkyl and chains, which may include one O, linking $R_1$ and $R_3$ to form pentosyl, hexosyl, cyclopentyl or cycohexyl rings, which rings optionally bear hydroxyl substituents; and M is H, $Na^+$, $K^+$, $NH_4^+$ or $N^+H_nR_{11(4-n)}$ where n is 0–3; and with the proviso that, when $R_6$ is an alkyl group, and R, $R_2$ and $R_4$ are H, $R_3$ is not H or methyl;

in admixture with a pharmaceutically acceptable carrier therefor.

6. The pharmaceutical composition of claim 5, where X is $C(O)$, $PO_2M$, $P(O)(OR_{14})$, $P(O)R_{13}$, SO, or $SO_2$.

7. A pharmaceutical composition comprising a nitrate ester having a formula selected from the group consisting of:

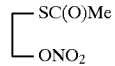

-continued

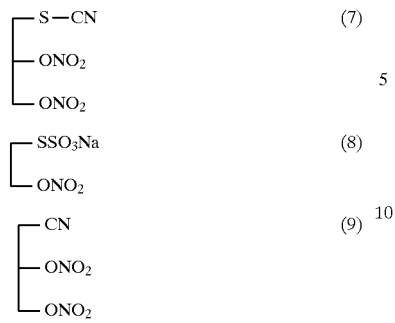

8. An aliphatic nitrate ester or salt thereof, containing at least one nitrate group, in which a S or P atom is situated β or γ to a nitrate group, or their congener, having a general formula:

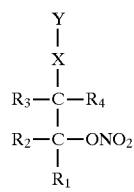

where X is $CH_2$, O, NH, S or $NCH_3$;

Y is SCN, $SCN_2H_2(R_5)_2$, $SC(O)NHR_5$, $SC(O)N(R_5)_2$, CN, $N_3$, $N_2H_2R_{13}$, $N_2HR_{13}R_{14}$, $CO_2M$, $CO_2H$, $CO_2R_{11}$, $C(O)R_{12}$, $C(O)(SR_{13})$;

$R_5$, $R_6$, $R_8$, $R_9$, $R_{10}$, $R_{12}$, $R_{13}$, $R_{14}$, $R_{15}$, $R_{16}$, are the same or different alkyls containing 1–12 carbon atoms which may contain 1–4 $ONO_2$ substituents or $C_1$ or $C_2$ connections to $R_1$–$R_3$ in cyclic derivatives;

$R_7$, $R_{11}$ are $C_1$–$C_8$, alkyl or acyl;

$R_2$ and $R_4$ are the same or different and selected from H, $ONO_2$, $C_1$–$C_4$ alkyl optionally bearing 1–3 nitrate groups, and acyl groups ($—C(O)R_{10}$);

$R_1$ and $R_3$ are the same or different and selected from H, $C_1$–$C_4$ alkyl and chains, which may include one O, linking $R_1$ and $R_3$ to form pentosyl, hexosyl, cyclopentyl or cycohexyl rings, which rings optionally bear hydroxyl substituents; and M is H, $Na^+$, $K^+$, $NH_4^+$ or $N^+H_nR_{11(4-n)}$ where n is 0–3; and with the proviso that, when X is O, Y is not $C(O)R_{12}$, and with the proviso that, when $R_5$ is an alkyl group, and R, $R_2$ and $R_4$ are H, $R_3$ is not H or methyl.

9. An aliphatic nitrate ester or salt thereof, containing at least one nitrate group, in which a S or P atom is situated β or γ to a nitrate group, or their congener, having a general formula:

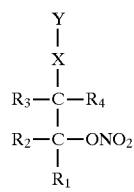

where X is SCN, $CH_2$, $SCN_2H_3(R_5)$, $C(O)$, $C(O)R_{12}$, $C(O)(OR_{13})$, $C(O)(SR_{13})$, or $NCH_3$;

Y is SCN, $SCN_2H_2(R_5)_2$, $CO_2R_{11}$, $C(O)R_{12}$, $C(O)(SR_{13})$, or does not exist;

$R_5$, $R_6$, $R_8$, $R_9$, $R_{10}$, $R_{12}$, $R_{13}$, $R_{14}$, $R_{15}$, $R_{16}$, are the same or different alkyls containing 1–12 carbon atoms which may contain 1–4 $ONO_2$ substituents or $C_1$ or $C_2$ connections to $R_1$–$R_3$ in cyclic derivatives;

$R_7$, $R_{11}$ are $C_1$–$C_8$, alkyl or acyl;

$R_2$ and $R_4$ are the same or different and selected from H, $ONO_2$, $C_1$–$C_4$ alkyl optionally bearing 1–3 nitrate groups, and acyl groups ($—C(O)R_{10}$);

$R_1$ and $R_3$ are the same or different and selected from H, $C_1$–$C_4$ alkyl and chains, which may include one O, linking $R_1$ and $R_3$ to form pentosyl, hexosyl, cyclopentyl or cycohexyl rings, which rings optionally bear hydroxyl substituents; and M is H, $Na^+$, $K^+$, $NH_4^+$ or $N^+H_nR_{11(4-n)}$ where n is 0–3; and with the proviso that, when $R_6$ is an alkyl group, and $R_1$ $R_2$ and $R_4$ are H, $R_3$ is not H or methyl.

10. A pharmaceutical composition comprising an effective amount of an aliphatic nitrate ester of claim 3 or a pharmaceutically acceptable salt thereof, in admixture with a pharmaceutically acceptable carrier therefor.

11. A pharmaceutical composition comprising an effective amount of an aliphatic nitrate ester of claim 8 or a pharmaceutically acceptable salt thereof, in admixture with a pharmaceutically acceptable carrier therefor.

12. A pharmaceutical composition comprising an effective amount of an aliphatic nitrate ester of claim 9 or a pharmaceutically acceptable salt thereof, in admixture with a pharmaceutically acceptable carrier therefor.

13. A method for making a nitrate ester having a formula selected from the group consisting of:

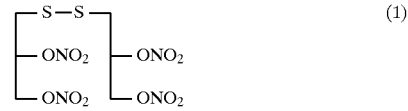

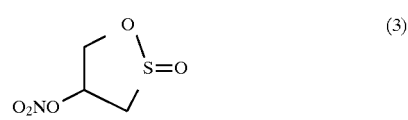

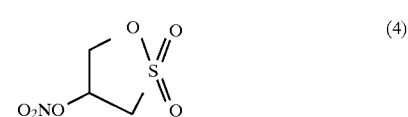

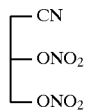 (9)

comprising; nitrating a corresponding substituted alcohol with a nitrating reagent, selected from a mixture of nitric acid and sulfuric acid in a mixture of water and an organic solvent, a nitrate salt and sulfuric acid in a mixture of water and an organic solvent, and nitronium tetrafluoroborate, and recovering therefrom the selected nitrate ester.

14. A method for making a nitrate ester having a formula selected from the group consisting of:

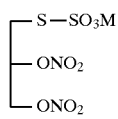 (2)

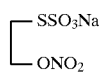 (8)

comprising, nitrating a corresponding halo-alkanol with a mixture of nitric acid and sulfuric acid in methylene dichloride and recovering therefrom a halo-alkyl nitrate; and reacting said halo-alkyl nitrate with $Na_2S_2O_3$ so as to produce the selected Bunte salt (2) or (8).

15. A method for making a nitrate ester having a formula:

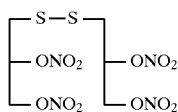 (1)

comprising: oxidizing said Bunte salt (2) of claim 14 and extracting said nitrate ester (1) therefrom.

16. A method for making a nitrate ester having a formula selected from the group consisting of:

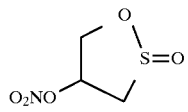 (3)

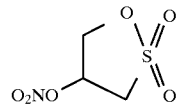 (4)

comprising: nitrating bis-(2, 3-dihydroxy propyl) disulfide in a mixture of aqueous nitric acid and sulfuric acid in methylene dichloride, and separating the desired product therefrom chromatographically.

17. A method for making a nitrate ester having a formula:

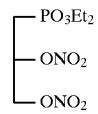 (5)

comprising: sllylating 3-bromopropane-1, 2-diol, treating said silyl ester with triethyl phosphite to produce a phosphonate, and nitrating said phosphonate to produce said nitrate ester.

18. A method for making a nitrate ester having a formula:

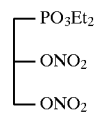 (5)

comprising: reacting triethyl phosphite with 1-bromo-2,3-epoxypropane to produce 1-phosphono-2,3-epoxypropane, and nitrating said 1-phosphono-2,3-epoxypropane to produce said nitrate ester.

19. A method for making a nitrate ester having a formula:

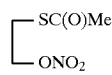 (6)

comprising: reacting a thioacetate salt with 2-bromoethyl nitrate to produce said nitrate monoester.

20. A method for making a nitrate ester having a formula:

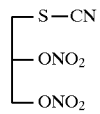 (7)

comprising: reacting a thiocyanate salt with 3-bromo-1, 2-propane dinitrate to produce said nitrate ester.

21. A method for making a nitrate ester having a formula:

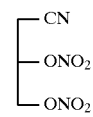 (9)

comprising: reacting a cyanide salt with 3-bromo-1, 2-propane dinitrate to produce said nitrate ester.

* * * * *

*UNITED STATES PATENT AND TRADEMARK OFFICE*

CERTIFICATE OF CORRECTION

PATENT NO.: 5,883,122          Page 1 of 2

DATED: March 16, 1999

INVENTORS: Thatcher, G.R.J., *et al.*

It is certified that errors appear in the above-identified patent and that said Letters Patent is hereby corrected as shown below:

On the face page, first column, [63], "Continuation-in-part of Ser. No. 658,145, filed as PCT/CA97/00372, May 30, 1997, Pat. No. 5,807,847" should be --Continuation-in-part of Ser. No. 658,145, filed June 4, 1996, Pat. No. 5,807,847--.

On the face page, first column, should appear --[30] Foreign Application Priority Data    May 30, 1997    [WO] WIPO .... PCT/CA97/00372--.

Column 1, lines 7-8, "Serial No. 08/658,145, filed as PCT/CA97/00372, May 30, 1997, now U.S. Pat. No. 5,807,847" should be --Serial No. 08/658,145, filed June 4, 1996, now U.S. Pat. No. 5,807,847--.

Column 2, line 44, "$S_2$" should be --$SO_2$--.

Column 4, line 56, "DTF" should be --DTT--.

Column 6, line 41, "Iosartan" should be --losartan--.

Column 7, line 19, "$N^+H_nR^{11(4-n)}$" should be --$N^+H_nR_{11(4-n)}$--.

Column 11, line 27, "aL" should be --al.--.

In claim 1, column 13, line 56, "when $R_5$ is an alkyl group" should be --when $R_6$ is an alkyl group--.

UNITED STATES PATENT AND TRADEMARK OFFICE
CERTIFICATE OF CORRECTION

PATENT NO.: 5,883,122

DATED: March 16, 1999

INVENTORS: Thatcher, G.R.J., *et al.*

It is certified that errors appear in the above-identified patent and that said Letters Patent is hereby corrected as shown below:

In claim 7, column 15, line 14, after 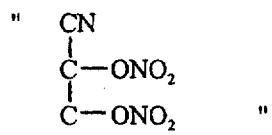 should be --in admixture with a pharmaceutically acceptable carrier therefor.--.

In claim 8, column 15, line 47, "$C(O)R_{i2}$" should be --$C(O)R_{12}$--.

In claim 8, column 15, line 48, "when $R_5$ is an alkyl group" should be --when $R_6$ is alkyl group --.

In claim 17, column 18, line 10, "sllylating" should be --silylating--.

Signed and Sealed this

Twenty-eighth Day of September, 1999

Attest:

Q. TODD DICKINSON

*Attesting Officer*   *Acting Commissioner of Patents and Trademarks*